United States Patent
Wilkie et al.

(10) Patent No.: US 10,918,690 B2
(45) Date of Patent: Feb. 16, 2021

(54) APPARATUS AND METHOD FOR PROCESSING ORGANIC BAMBOO LEAF EXTRACT PRODUCTS

(71) Applicants: Louise Wilkie, Surrey (CA); Jacqueline Wilkie, Surrey (CA)

(72) Inventors: Louise Wilkie, Surrey (CA); Jacqueline Wilkie, Surrey (CA)

( * ) Notice: Subject to any disclaimer, the term of this patent is extended or adjusted under 35 U.S.C. 154(b) by 0 days.

(21) Appl. No.: 16/377,201

(22) Filed: Apr. 6, 2019

(65) Prior Publication Data
US 2020/0078433 A1    Mar. 12, 2020

Related U.S. Application Data

(63) Continuation-in-part of application No. 16/124,128, filed on Sep. 6, 2018, now Pat. No. 10,421,670.

(51) Int. Cl.
*A61K 36/89* (2006.01)
*A23L 33/10* (2016.01)
(Continued)

(52) U.S. Cl.
CPC .............. *A61K 36/899* (2013.01); *A23L 2/38* (2013.01); *A23L 2/72* (2013.01); *A23L 3/001* (2013.01);
(Continued)

(58) Field of Classification Search
CPC .. C02F 1/265; C02F 1/30; C02F 1/004; C02F 2103/08; C02F 2303/04; C02F 2101/14; C02F 2209/06; C02F 2209/02; C02F 2103/26; C02F 2103/10; C02F 2103/007; C02F 1/008; C02F 1/02; C02F 1/32; C02F 1/68; C02F 1/685; C02F 1/686; C02F 1/78; C02F 9/00; C02F 2209/36; A23L 3/003;
(Continued)

(56) References Cited

U.S. PATENT DOCUMENTS 2,033,326 A * 3/1936 Clark ........................ C12C 7/28
426/29
5,466,453 A * 11/1995 Uchida .................... A23G 4/06
424/735
(Continued)

OTHER PUBLICATIONS

Derwent Translated Abstract for Patent Publication CN 107455631, Chen Z. et al, published Dec. 12, 2017. (Year: 2017).*
(Continued)

*Primary Examiner* — Joseph W Drodge
(74) *Attorney, Agent, or Firm* — Edmond DeFrank

(57) ABSTRACT

The embodiments disclose a method including harvesting fresh bamboo leaves from an organic certified bamboo forest, using hot air to sterilize and dry bamboo leaves, shredding and packing the dry bamboo leaves, mixing sterilized water steam and the shredded dry bamboo leaves for extracting the dry bamboo leaves essence into a bamboo leaf condensate, filtering the bamboo leaf condensate through sterile filters and devices, mixing in purified water and additives to the filtered bamboo leaf condensate for creating bamboo leaf extract based products for human consumption and use, and packaging the bamboo leaf extract based products including bottled beverages, cosmetics, pharmaceuticals, and foods, food additives and dietary supplements.

15 Claims, 16 Drawing Sheets

(51) Int. Cl.
  *A23L 3/00* (2006.01)
  *A23L 3/40* (2006.01)
  *A23L 2/38* (2006.01)
  *A23L 2/72* (2006.01)
  *B01D 11/02* (2006.01)
  *B01D 36/02* (2006.01)
  *C12G 3/05* (2019.01)
  *C12G 3/06* (2006.01)
  *A61K 8/97* (2017.01)
  *A61K 36/899* (2006.01)
  *G06Q 50/02* (2012.01)
  *G16B 50/30* (2019.01)
  *A23L 33/105* (2016.01)
  *A23L 3/005* (2006.01)
  *C12G 3/055* (2019.01)

(52) U.S. Cl.
  CPC ............. *A23L 3/005* (2013.01); *A23L 3/40* (2013.01); *A23L 33/105* (2016.08); *A61K 8/97* (2013.01); *B01D 11/0288* (2013.01); *B01D 36/02* (2013.01); *C12G 3/055* (2019.02); *C12G 3/06* (2013.01); *G06Q 50/02* (2013.01); *G16B 50/30* (2019.02)

(58) Field of Classification Search
  CPC ... A23L 2/72; A23L 3/00; A23L 3/001; A23L 3/005; A23L 3/3409; A23L 3/3418; A23L 2/38; A23L 2/42; A23L 2/48; A23L 2/50; A23L 2/52; A23L 2/60; A23L 2/68; A23L 2/78; A23L 33/105; A23L 3/40; B67C 7/0073; B67C 3/007; B67C 3/0073; B67C 2003/228; A61K 33/00; A61K 31/185; A61K 31/19; A61K 36/00; A61K 36/899; A61K 8/97; C12G 3/04; C12G 3/08; C12G 3/085; C12G 3/05; C12G 3/055; C12G 3/06; C12C 12/00; C12C 12/002; A61L 2/0017; A61L 2/0023; A61L 2/0047; A61L 2/02; A61L 2/022; A61L 2/04; A61L 2/08; A61L 2/10; A61L 2/28; G16B 50/30; G06Q 50/02; B01D 1/00; B01D 5/00; B01D 11/0207; B01D 11/0288; B01D 11/028; B01D 29/00; B01D 29/0047; B01D 29/0052; B01D 29/0059; B01D 29/60; B01D 36/00; B01D 36/02
  USPC ......... 210/85, 134, 143, 149, 175, 192, 335, 210/739, 764, 767, 774; 159/47.1; 424/725, 750; 426/419, 481, 615; 422/2, 422/3, 14, 22, 24, 28, 29, 40, 41
  See application file for complete search history.

(56) References Cited

U.S. PATENT DOCUMENTS

| | | | | |
|---|---|---|---|---|
| 6,268,353 | B1* | 7/2001 | Chaen | A21D 2/16 514/53 |
| 8,519,296 | B2* | 8/2013 | Tricarico | B23H 7/18 219/69.16 |
| 2001/0002269 | A1* | 5/2001 | Zhao | A23F 5/44 426/112 |
| 2003/0228393 | A1* | 12/2003 | Zhao | A23L 2/56 426/74 |
| 2004/0219574 | A1* | 11/2004 | Beimfohr | C12Q 1/689 435/6.13 |
| 2005/0136133 | A1* | 6/2005 | Imamura | A61P 1/16 424/725.1 |
| 2006/0062890 | A1* | 3/2006 | Delgado Araujo | A23L 11/33 426/634 |
| 2006/0078632 | A1* | 4/2006 | Woo | A61P 31/12 424/750 |
| 2007/0129430 | A1* | 6/2007 | Miyata | A23K 20/158 514/474 |
| 2007/0248693 | A1* | 10/2007 | Mazzio | A61K 36/8895 424/725 |
| 2008/0050500 | A1* | 2/2008 | Muranishi | A23L 2/56 426/590 |
| 2008/0107760 | A1* | 5/2008 | Kusaka | A23L 33/105 424/750 |
| 2008/0233242 | A1* | 9/2008 | Zhang | A23L 2/44 426/72 |
| 2009/0169679 | A1* | 7/2009 | Deka | A23F 3/166 426/50 |
| 2010/0233348 | A1* | 9/2010 | Watanabe | C11B 9/02 426/651 |
| 2014/0234488 | A1* | 8/2014 | Chang | A23L 2/38 426/62 |
| 2014/0322260 | A1* | 10/2014 | Tani | A61K 36/185 424/195.15 |
| 2018/0208387 | A1* | 7/2018 | Cantrell | B65D 33/002 |
| 2019/0136168 | A1* | 5/2019 | Tegtmeier | C12H 1/0408 |

OTHER PUBLICATIONS

Derwent Translated Abstract for Patent Publication CN 102224969, Liu H, published May 27, 2011. (Year: 2011).*
Derwent Translated Abstract for Patent Publication CN 102144685, Ge X, published Aug. 10, 2011. (Year: 2011).*
Derwent Translated Abstract for Patent Publication CN 106721778, Chen Z. et al, published May 31, 2017. (Year: 2017).*

* cited by examiner

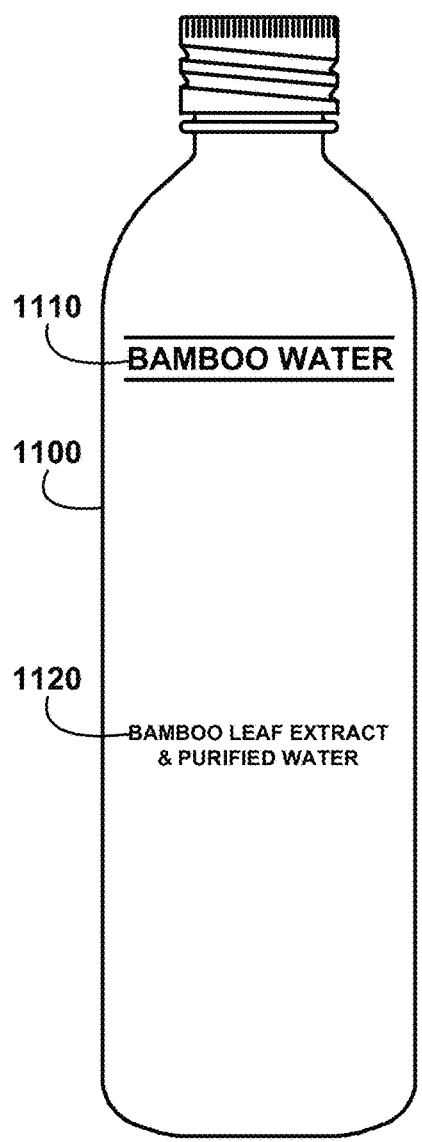
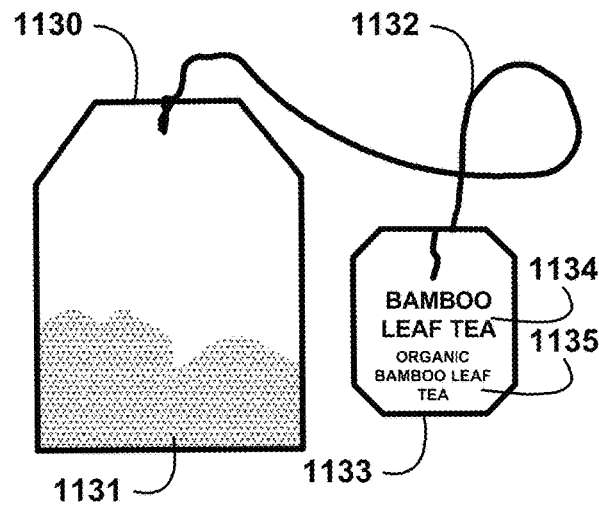
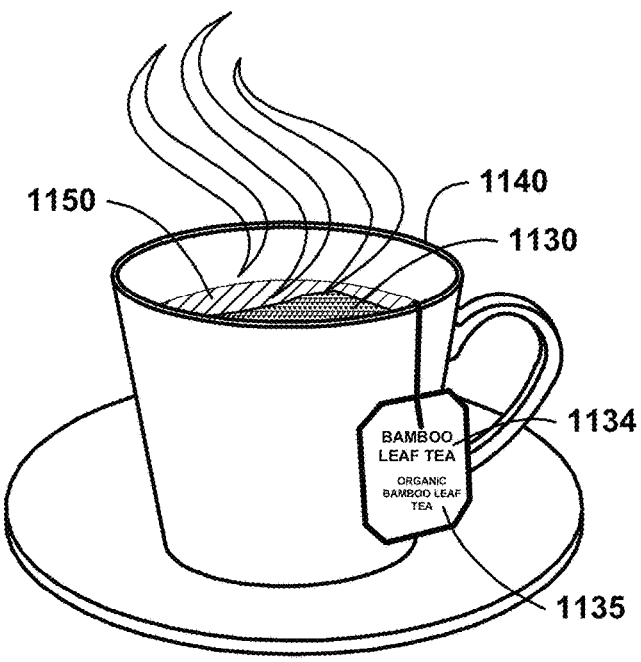
FIG. 11A
FIG. 11B
FIG. 11C

APPARATUS AND METHOD FOR PROCESSING ORGANIC BAMBOO LEAF EXTRACT PRODUCTS

CROSS-REFERENCE TO RELATED APPLICATIONS

This patent application is a Continuation-in part and claims priority to United States patent application entitled: "HUMIC AND FULVIC BLACK WATER BASED BEVERAGE FOR HUMAN CONSUMPTION", U.S. Ser. No. 16/124,128 filed on Sep. 6, 2018, the U.S. patent application being incorporated herein by reference.

BACKGROUND

Consumers have undergone some recent changes in their desire to consume and use products that are free of harmful chemicals, non-natural ingredients, and over processed products that can have diminished health benefits. This is evident in consumer backlash at GMO foods, high fructose corn syrup foods and beverages, synthesized ingredients in pharmaceutical and cosmetic products and other non-natural non-sustainable products and processing methods. Different cultures around the world may be familiar with natural ingredients from their local regions that other cultures in many cases are only now becoming aware of those natural ingredients. The globalization of businesses has now facilitated the globalization of cross-cultural awareness of those regional natural ingredients and the potential health benefits of the products that can be made using those natural ingredients in a sustainable consumptive method.

BRIEF DESCRIPTION OF THE DRAWINGS

FIG. 11A shows for illustrative purposes only an example of a bottled bamboo water of one embodiment.

FIG. 11B shows for illustrative purposes only an example of bamboo leaf tea bag of one embodiment.

FIG. 11C shows for illustrative purposes only an example of a bamboo tea beverage of one embodiment.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the embodiments.

General Overview:

It should be noted that the descriptions that follow, for example, in terms of apparatus and method for processing organic bamboo leaf extract products is described for illustrative purposes and the underlying system can apply to any number and multiple types beverages and human consumables. In one embodiment of the present invention, the apparatus and method for processing organic bamboo leaf extract products can be configured using certified organic bamboo leaves. The apparatus and method for processing organic bamboo leaf extract products can be configured to include purified water and can be configured to include additives using the embodiments.

Figure 1:
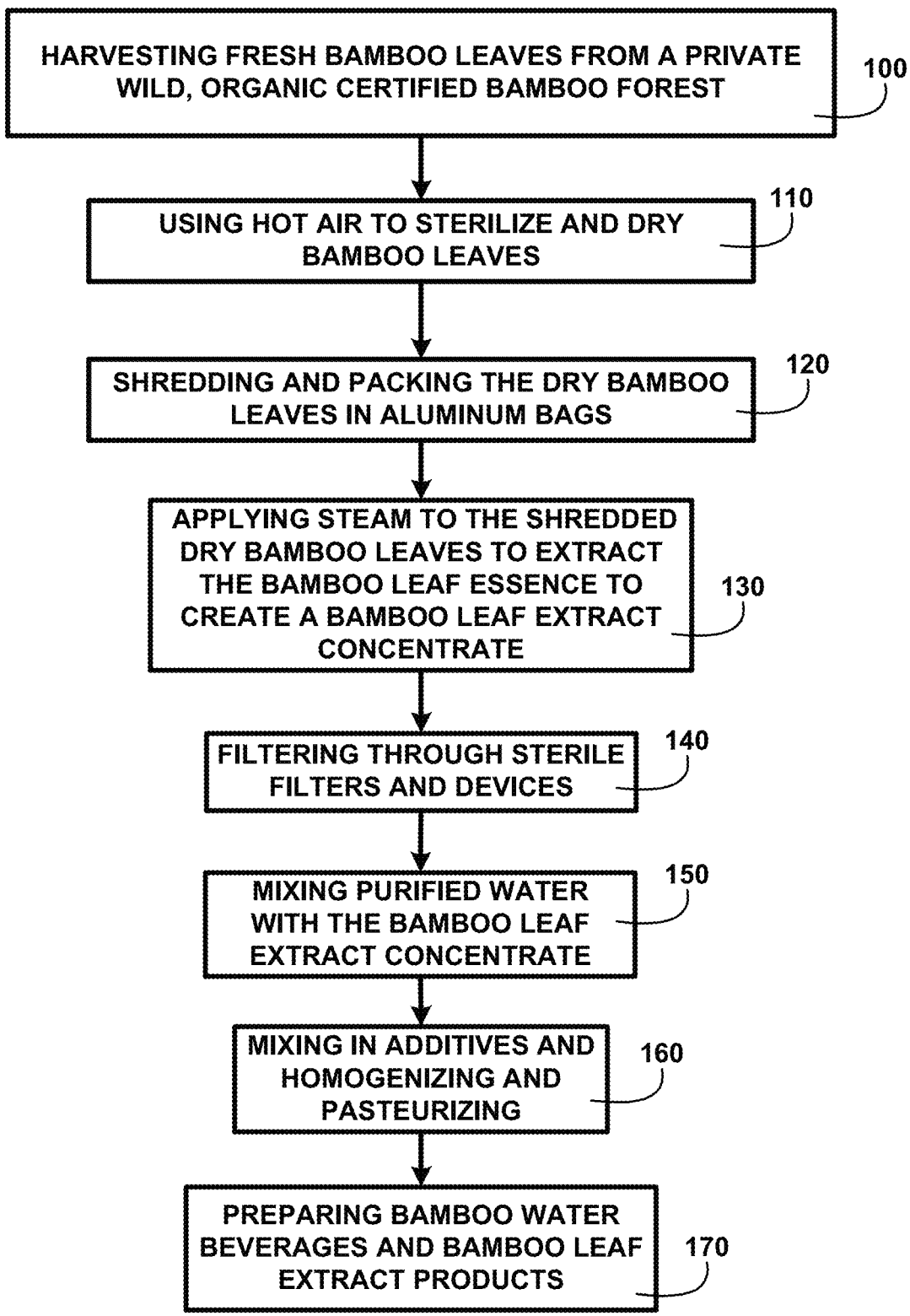
FIG. 1 shows a block diagram of an overview of apparatus and method for processing bamboo leaf extract products of one embodiment.

FIG. 1 shows a block diagram of an overview of apparatus and method for processing bamboo leaf extract products of one embodiment. FIG. 1 shows a process of harvesting fresh bamboo leaves from a private wild, organic certified bamboo forest 100 and using hot air to sterilize and dry bamboo leaves 110. Processing includes shredding and packing the dry bamboo leaves in aluminum bags 120. The process includes applying and mixing sterilized water steam to the shredded dry bamboo leaves to extract the bamboo leaf essence to create a bamboo leaf extract condensate 130. An extraction machine is used for generating and conveying a sterilized water steam vapor for the application process and includes sensors and digital controllers to regulate the temperature of the sterilized water steam to maintain a sterilized condition to create an aseptic extraction environment free from contamination caused by harmful bacteria, viruses, spores and other microorganisms. The extraction machine includes a condensing device to condense bamboo leaf essence vapors to create a bamboo leaf extract condensate. The bamboo leaf extract condensate under goes filtering through sterile filters and devices 140. The filtering process is followed by mixing purified water with the bamboo leaf extract condensate 150. Mixing in additives and homogenizing 160 to the bamboo leaf extract and purified water mixture continues processing for preparing bamboo water beverages and bamboo leaf extract products 170 of one embodiment.

Figure 2A:
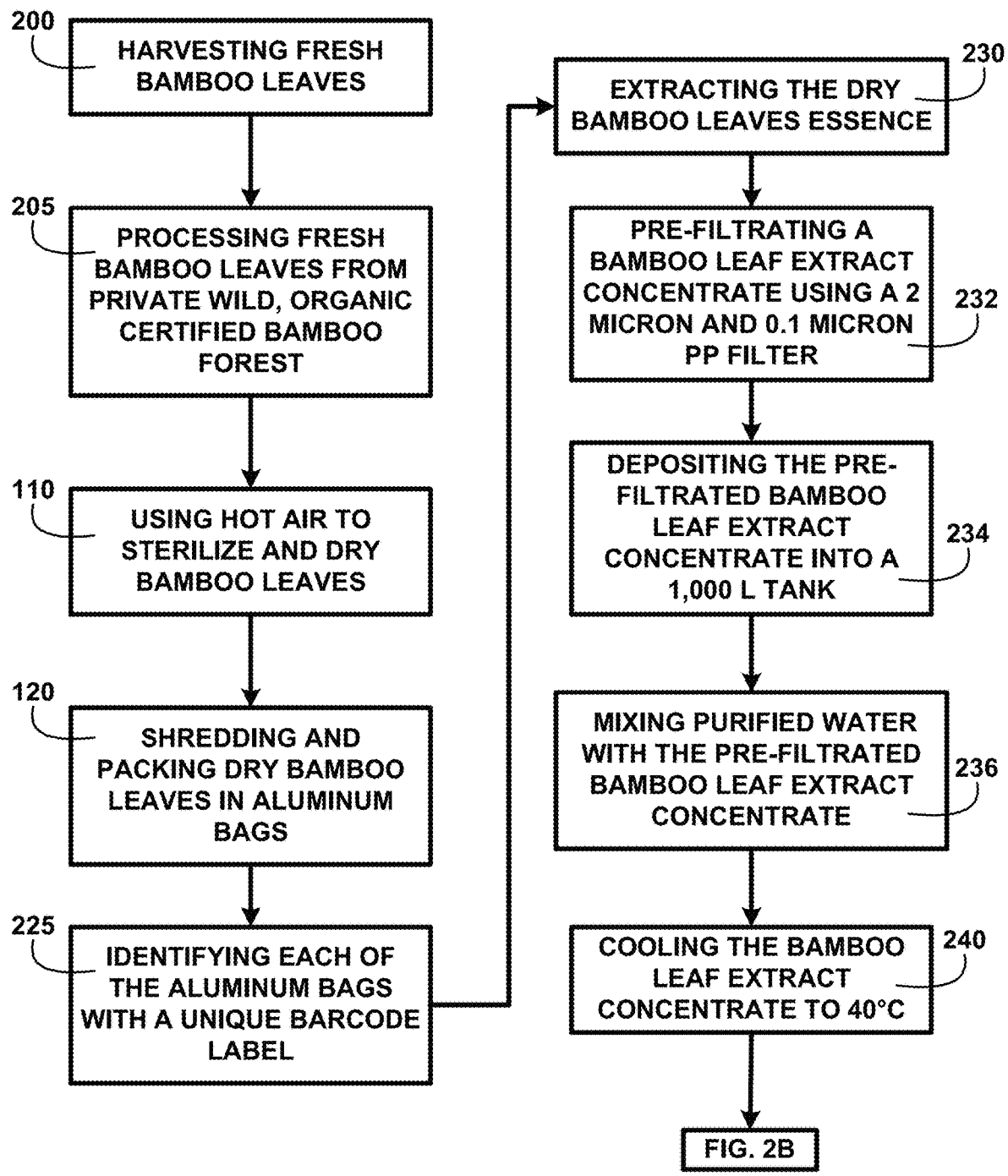
FIG. 2A shows a block diagram of an overview flow chart of harvesting fresh bamboo leaves of one embodiment.

Detailed Description:

FIG. 2A shows a block diagram of an overview flow chart of harvesting fresh bamboo leaves of one embodiment. FIG. 2A shows a first process of harvesting fresh bamboo leaves 200 and processing fresh bamboo leaves from private wild, organic certified bamboo forest 205. Quality control begins with using hot air to sterilize and dry bamboo leaves 110. Shredding and packing the dry bamboo leaves in aluminum bags 120 is a preparation process. Identifying each of the aluminum bags with a unique barcode label 225 allows tracking of the product ingredients through the processing. Extracting the dry bamboo leaves essence 230 concentrates the beneficial properties contained in bamboo. The extraction process treats the shredded dry bamboo leaves with sterilized water steam and condensing the bamboo extract vapors to create a bamboo leaf extract condensate. Filtering the bamboo leaf extract condensate using a 2 micron and 0.1 micron pp filter 232 removes any residual particulates. Depositing the pre-filtered bamboo leaf extract condensate into a 1,000 l tank 234 is followed with mixing purified water with the pre-filtered bamboo leaf extract condensate 236 then cooling the bamboo leaf extract condensate to 40° C. 240 of one embodiment.

The health benefits of bamboo include healthy weight loss, balanced cholesterol levels, and a boosted immune system. They also have cancer-fighting and anti-inflammatory properties, are heart-friendly, contain protein, vitamins and minerals, and a negligible amount of fat. Bamboo sap is the liquid which comes from bamboo plants. The sap has vital nutrients to make the tree grow and it is also beneficial for the human body. It has a diuretic effect and relaxes the body and mind. It is considered a health tonic, and an aid to complexion. Bamboo sap is rich in calcium and amino acids. In Chinese medicine, it was believed to be good treatment for freckles, age spots, fever, phlegm, high blood pressure and poor eyesight. Bamboo extract contains bamboo sap.

Bamboo sap products have been used for agricultural pesticides, enhance sugar content or to help plants ripen well. Lately, it has been used in animal feed for pigs and cows. Soaps containing bamboo sap are popular as it helps keep skin moist, is good for washing and helps skin conditions including atopy, and has an effect of drawing waste products from the skin. Bamboo extract contains bamboo salt is considered a precious medicine because it has special medical action such as general wellbeing, detoxication and stimulating appetite. Bamboo salt is used in cooking, with its special taste and health benefits. It can replace regular salt in making soy sauce, bean paste and pepper paste. It is also used in skin care because it makes skin softer during washing. Placing one's feet in water with this salt is known to ease tiredness. It is also used in toothpaste.

The bamboo leaf extract is suitable for cosmetic products including for example skin moisturizers, perfumes, lipsticks, fingernail polishes, eye and facial makeup preparations, cleansing shampoos, permanent waves, hair colors and deodorants and other components used in cosmetic products. Hemp and medicinal legalized CBD and medicinal legalized cannabis can be used in the solution for the human consumption beverages and the human use topical products for medicinal reasons. The bamboo leaf extract is suitable for pharmacological products including for example sunscreen creams and lotions, first aid topical creams including topical agents to enhance healing of wounds infected with drug-resistant pathogens; and incorporating malacidins to attack and kill many types of super bugs, such as methicillin-resistant *Staphylococcus aureus* (MRSA) of one embodiment.

The mixture of ingredients is processed by treating the purified aqueous ingredient mixture including sterilizing, adjusting the pH level, dechlorinating, defluoridating, filtering particulates, and desalinating. The bamboo leaf extract condensate in an aqueous solution is used for creating a bamboo water beverage, flavored beverages, soft drinks, alcoholic beverages, supplements and food additives using a mixture of bamboo leaf extract ingredients of one embodiment. A beverage is processed and treated with the bamboo leaf extract suspended within purified water to create bamboo water.

Bamboo Leaf Extract Cosmetic Products:

The bamboo leaf extract condensate is suitable for cosmetic products including for example skin moisturizers, perfumes, lipsticks, fingernail polishes, eye and facial makeup preparations, cleansing shampoos, permanent waves, hair colors and deodorants and other components used in cosmetic products. The bamboo leaf extract cosmetic products can include pharmacological components for example incorporating malacidins and other antibiotic agents to enhance healing of wounds, skin irritants and infections of one embodiment.

Bamboo Leaf Extract Pharmacological Products:

The bamboo leaf extract condensate is suitable for pharmacological products including for example sunscreen creams and lotions, first aid topical creams including topical agents to enhance healing of wounds infected with drug-resistant pathogens; and incorporating malacidins to attack and kill many types of super bugs, such as methicillin-resistant *Staphylococcus aureus* (MRSA) and other antibiotic agents to enhance healing of wounds, skin irritants and infections of one embodiment.

Products for Human Consumption and Use:

Combining predetermined quantities of additive ingredients with bamboo leaf extract condensate includes adding de-ionized purified water and adding carbonation. Combining ingredients for alcoholic beverages includes adding at least one alcoholic drink ingredient for example vodka, tequila, gin, rum, brandy and other distilled alcoholic spirits to the suspended aqueous bamboo leaf extract condensate. At least one temperature regulating device is configured to chill an alcohol beverage ingredient and a mesh at a predetermined size for filtering the chilled alcohol ingredient to capture flock to prevent clouding. An alcohol ingredient is cut with sanitized and purified water with suspended aqueous bamboo leaf extract to not less than a 40% alcohol by volume (ABV) the legal minimum for an alcohol neutral spirits and alcohol labeled beverage.

Bamboo water alcoholic beverages will include a flavoring based on the type of alcohol added to the mix including beers, wines, distilled liquors and alcohol neutral spirits. Bamboo leaf extract will be conveyed to the bottling processes through a separate discharge piping system. Alcoholic beverages will be mixed with the bamboo leaf extract in predetermined volumes of one embodiment.

The processes of combining predetermined quantities of additive ingredients are followed by processes for creating products for human consumption including bamboo water beverages, flavored beverages, effervescent flavored beverages, alcoholic beverages, supplements, food additives, and zero calorie beverages.

Combinations of the ingredients can produce different tastes and consumer benefits including found in bones, skin, and teeth, and flavonoids, plant-based antioxidants and other benefits. Combining quantities of additive ingredients and selecting some but not all of the ingredients are varied to target specific benefits and taste in the products for human consumption. The bamboo leaf extract does not include harmful chemicals and other chemicals that can pose a health risk to consumers are not used in the extraction, mixing and bottling processes. At least annually sample(s)

consisting of primary containers of product of unit packages of product shall be tested by an approved competent commercial laboratory and the results of the at least annual test results will be keep on file and logged into a bamboo water bottling process server of one embodiment.

Artificial Sweetener Ingredients:

Bamboo water beverages may include an artificial sweetener additive ingredient used for creating products for human consumption. The artificial sweetener additive ingredients include aspartame, sucralose, neotame, and other artificial sweeteners of one embodiment.

Natural Sweetener Ingredients:

Bamboo water beverages may include a natural sweetener additive ingredient used for creating products for human consumption. The natural sweetener additive ingredients include *stevia* leaf extract, sweet proteins, synsepalum dulcificum berry, rebaudioside, erythritol, monk fruit, inulins, alcohol sugars, and other natural sweeteners. Some of the natural sweetener additive ingredients have no or low levels of calories. The inulin group of natural sweetener additive ingredients includes chicory root, agave, Jerusalem artichoke and other inulin sources.

Inulin is not digested or absorbed in the stomach. It goes to the bowels where beneficial bacteria are able to use it to grow. It supports the growth of a special kind of bacteria that are associated with improving bowel function and general health. Inulin decreases the body's ability to make certain kinds of fats. Inulin received no-objection status as generally recognized as safe (GRAS) from the US Food and Drug Administration (FDA). Inulin is not digested by enzymes in the human alimentary system, contributing to its functional properties: reduced calorie value, dietary fiber and prebiotic effects of one embodiment.

Bamboo Extract and Bamboo Essence:

Bamboo extract is light green or green-brown in color and bamboo essence can be a yellow or yellow-brown liquid. Both are obtained from bamboo and can lower fever, reduce a sense of nausea and release phlegm. They are used to aid paralysis and epilepsy. The extract has similar effects to the essence. Bamboo essence is beneficial against strokes, stuffiness in the chest, paralysis, speech impediments, diabetes, tetanus, pyrexia and infant epilepsy, and is recanted in Respected Chinese medical books as necessary medicine to treat palsy, speech impediments, and half-body paralysis.

Bamboo extract contains various components including proteins, carbohydrates, minerals, and are low in fat and sugars. A 100 gram serving of bamboo extract contains only 20 calories. The carbohydrates do not amount to more than 3-4 grams per 100-gram serving. The amount of sugar found in bamboo is about 2.5 grams per 100-gram serving. This is less than the amount of sugar found in many fruits and vegetables. A serving of 100 grams of bamboo contains less than 0.49 grams of fat. This fat consists of both saturated and unsaturated fats. Unsaturated fats are needed by the body as they control the spread of (bad) LDL cholesterol throughout the body. A 100 gram serving of bamboo shoots would have about 2 to 2.5 grams of protein. The proteins found in bamboo consist of seventeen essential amino acids and two semi-essential amino acids.

The bamboo leaf extract condensate contains amino acids, calcium, carbohydrate, fats, iron, magnesium, phosphorus, potassium, protein, sodium, vitamin C, vitamin E, tyrosine and other elements and compounds. Bamboo contains generally tyrosine, arginine histidine, and leucine as amino acids. The presence of tyrosine facilitates biochemical metabolism of our body as it is a major constituent of adrenals which are precursors for adrenaline, necessary for active body metabolic activities. It also plays important role in function of thyroid and pituitary glands which are involved in producing and regulating hormones in human body. Presence of phytosterols in bamboo reduces fat and cholesterol levels of blood making them one of the most sought after health foods among patients with life style related disorders. A survey conducted showed that some ethnic tribes of Northeast India used bamboo to control high blood pressure and cardiovascular ailments.

Another study shows that a diet containing bamboo had reducing effect on serum content of total cholesterol and low density lipoprotein. There was increase in the frequency of bowel movement and fecal volume indicating its role in cholesterol lowering and diabetes prevention in individuals provided with bamboo diets. There are reported instances of using bamboo by Karbi Anglong tribes of India to control early stage of cancer. The anticancer property of bamboo might be attributed to the presence of lignans and phytosterols. The production of carcinogens, growth of cancer cells, cell invasion, and metastasis are inhibited by phytosterol. Regular intake of bamboo reduces reproductive health related problems in female. Bamboo is used by local tribes belonging to Bodo, Thadau, Mosang, and Tiwa for treatment of irregular menstrual cycle, heavy bleeding after delivery, infertility problems, reducing labor pain, and also for inducing puberty in young females.

Bamboo contains vitamins such as vitamin A, vitamin B6, vitamin E, thiamin, riboflavin, niacin, folate, and pantothenic acid. Minerals found in bamboo include calcium, magnesium, phosphorus, potassium, sodium, zinc, copper, manganese, selenium and iron. Bamboo is weight loss-friendly. The number of calories, carbohydrates, and sugars contained in bamboo is almost negligible. Bamboo is an ideal food for people who want to lose weight and also want their stomachs to feel full. Bamboo is used in dissolving harmful LDL cholesterol in the body. This eases cholesterol out of the arteries for a smooth supply and movement of blood throughout the body.

Consumption of bamboo products is also helpful in decreasing LDL cholesterol levels, with stable glucose levels and has favorable effects on cholesterol, lipids, and bowel function. Studies conducted on bamboo have indicated that leaves of bamboo consist of phytosterols such as flavone, amylase, and chlorophyll. Out of these, chlorophyll showed properties of controlling mutations and cancer. The vitamins, minerals, and antioxidants present in bamboo are ideal for improving the body's immune system. Bamboo constituents promote anti-inflammatory and analgesic (pain-killing) properties and include a beneficial effective against respiratory disorders.

Bamboo consumption is useful in treating stomach disorders and bamboo leaves are also suggested as a remedy for intestinal worms. Bamboo has a high amount of potassium. Potassium is highly beneficial as an electrolyte and is also very good for lowering and maintaining blood pressure. The presence of high content of protein, amino acids, minerals, fiber, carbohydrates, and low fat makes the bamboo one of the widely acclaimed nutrient rich food items. Also the presence of phytosterols in young shoots provides youthful feeling, athletic energy, and longevity to regular consumers. Bamboo is being used as an important health food as bamboo contains proteins, amino acids, carbohydrates, many important minerals, and vitamins. Freshly collected bamboo contains amounts of thiamine, niacin, vitamin A, vitamin B6, and vitamin E. The know records of the effects and health benefits of bamboo have been written about since at least 618 AD. The processing continues and is further described in FIG. 2B.

Figure 2B:
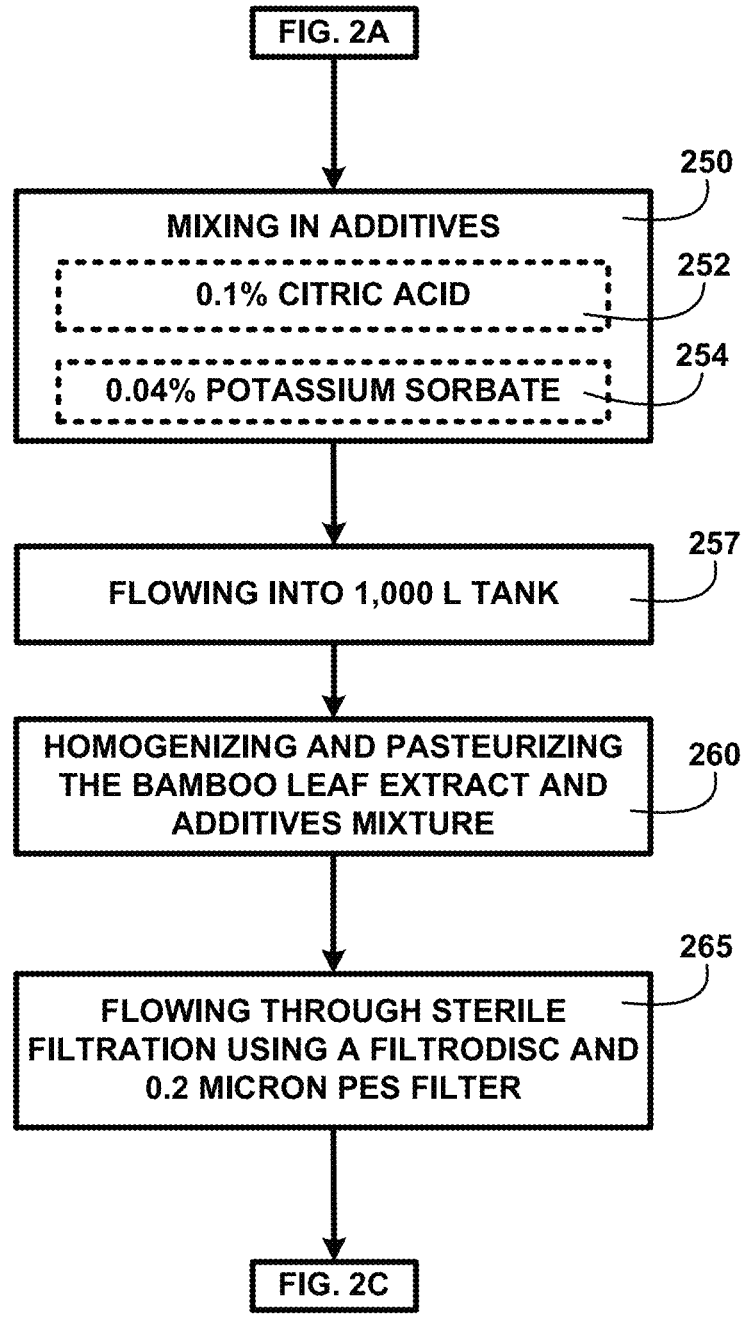
FIG. 2B shows a block diagram of an overview flow chart of mixing in additives of one embodiment.

Mixing in Additives:

FIG. 2B shows for illustrative purposes only an example of mixing in additives of one embodiment. FIG. 2B shows a continuation from FIG. 2A with processes including mixing in additives 250 including 0.1% citric acid 252 and 0.04% potassium sorbate 254. Other additives can include antibiotic free, non-GMO natural ingredients, including proteins, isotonic solutions, CBD and hemp, caffeine, fulvic and humic acids, alcohol-liquor, tea, coffee, sparkling water, carbonation, fruit flavorings, citric juices, natural flavorings, cane sugar, natural additives, fruit juice additives, sugar additives like sucralose, *stevia*, artificial sweeteners, natural plant sweeteners and others. The bamboo water and additives mixtures are flowing into 1,000 l tank 257 storage for processes including homogenizing and pasteurizing the bamboo leaf extract and additives mixture 260 and flowing through sterile filtration using a filtrodisc and 0.2 micron pes filter 265. These processed mixtures are then prepared for creating bamboo leaf extract beverages including thirst quenching drinks, energy drinks, medicinal beverages, alcohol-liquor beverages and other bamboo leaf extract based products of one embodiment. Descriptions of other processes continue in FIG. 2C.

Figure 2C:
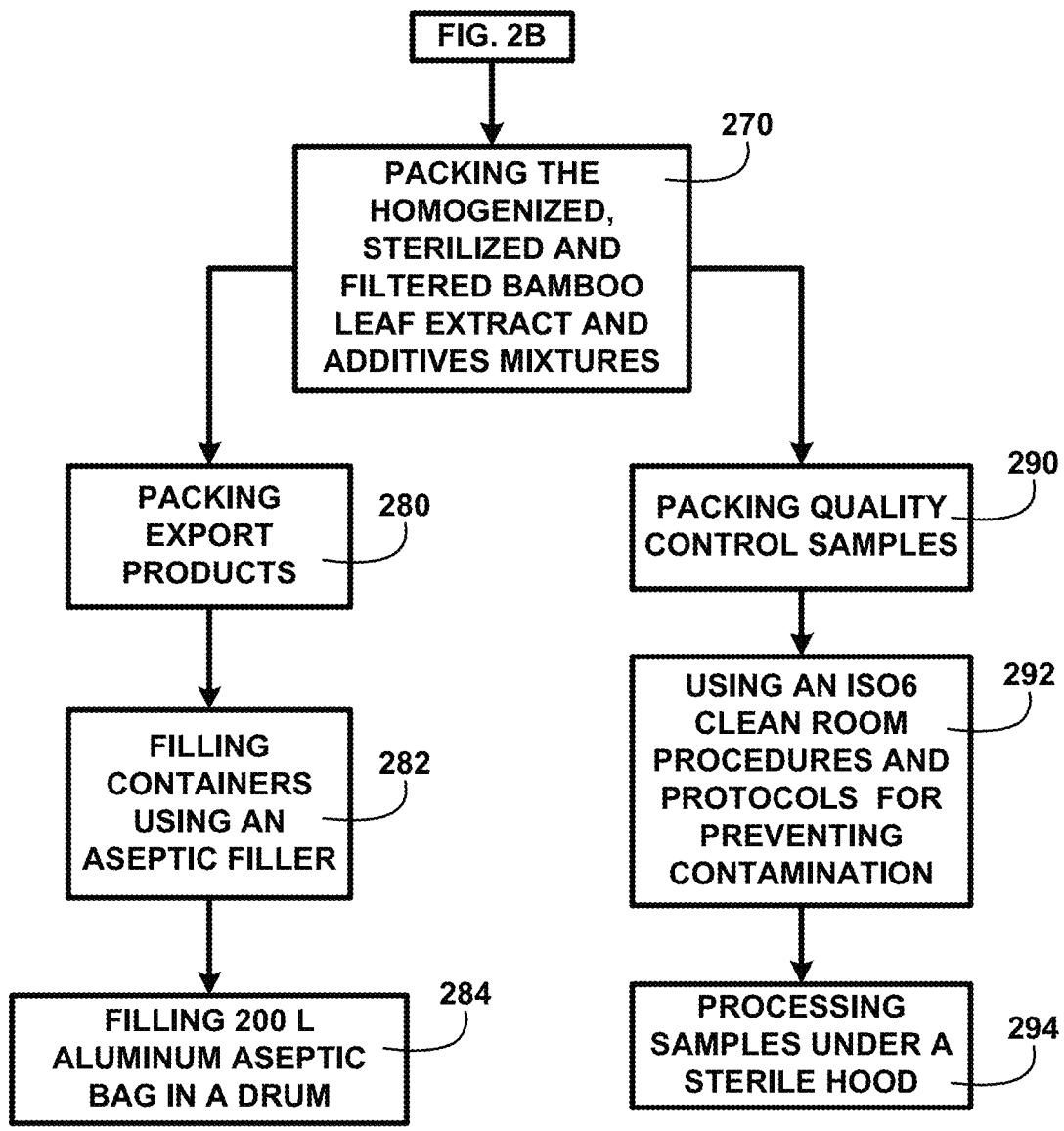
FIG. 2C shows a block diagram of an overview flow chart of packing the homogenized, sterilized and filtered bamboo leaves and additives mixture of one embodiment.

Packing the Homogenized, Sterilized and Filtered Bamboo Leaves and Additives Mixture:

FIG. 2C shows for illustrative purposes only an example of packing the homogenized, sterilized and filtered bamboo leaves and additives mixture of one embodiment. FIG. 2C shows continuing from FIG. 2B bamboo leaf extract product processing including packing the homogenized, sterilized and filtered bamboo leaf extract and additives mixtures 270. Bamboo leaf extract can be shipped as the condensate wherein packing export products 280 includes filling containers using an aseptic filler 282. The bamboo leaf extract condensate is processed for filling 200 l aluminum aseptic bag in a drum 284 for example for shipment to other countries for final product processing. Quality control measures include packing quality control samples 290 using an ISO6 clean room procedures and protocols for preventing contamination 292. Processing samples under a sterile hood 294 for inspection to assure all quality measures are being met during the various processes of one embodiment.

Figure 3:
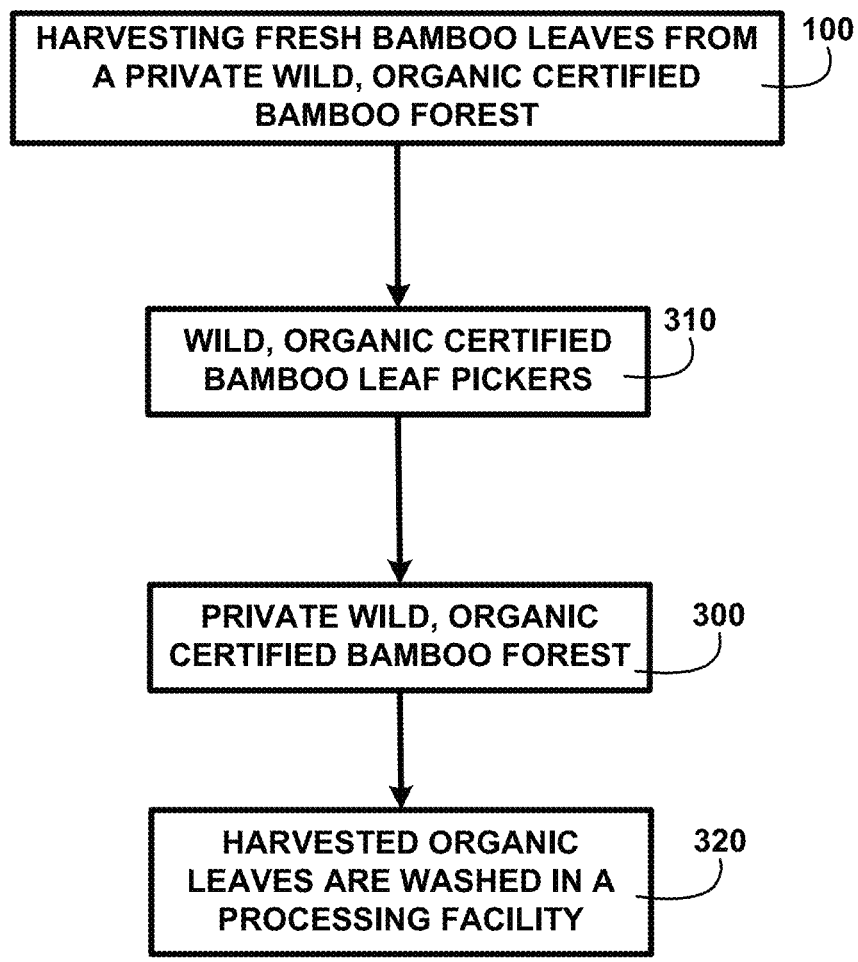
FIG. 3 a block diagram of an overview flow chart a block diagram of an overview flow chart of private wild organic certified bamboo forest of one embodiment.

Private Wild Organic Certified Bamboo Forest:

FIG. 3 shows a block diagram of an overview of private wild organic certified bamboo forest of one embodiment. FIG. 3 shows harvesting fresh bamboo leaves from a private wild, organic certified bamboo forest 100. Harvesting employs a group of wild, organic certified bamboo leaf pickers 310 who harvest the freshly sprouted bamboo leaves. The source of these bamboo leaves is a private wild, organic certified bamboo forest 300 where bamboo water leaves are obtained. The young leaves are harvested in a sustainable manner to protect the bamboo forest and assure an ongoing supply of this precious resource. Once picked, the harvested organic leaves are washed in a processing facility 320 of one embodiment.

Figure 4:
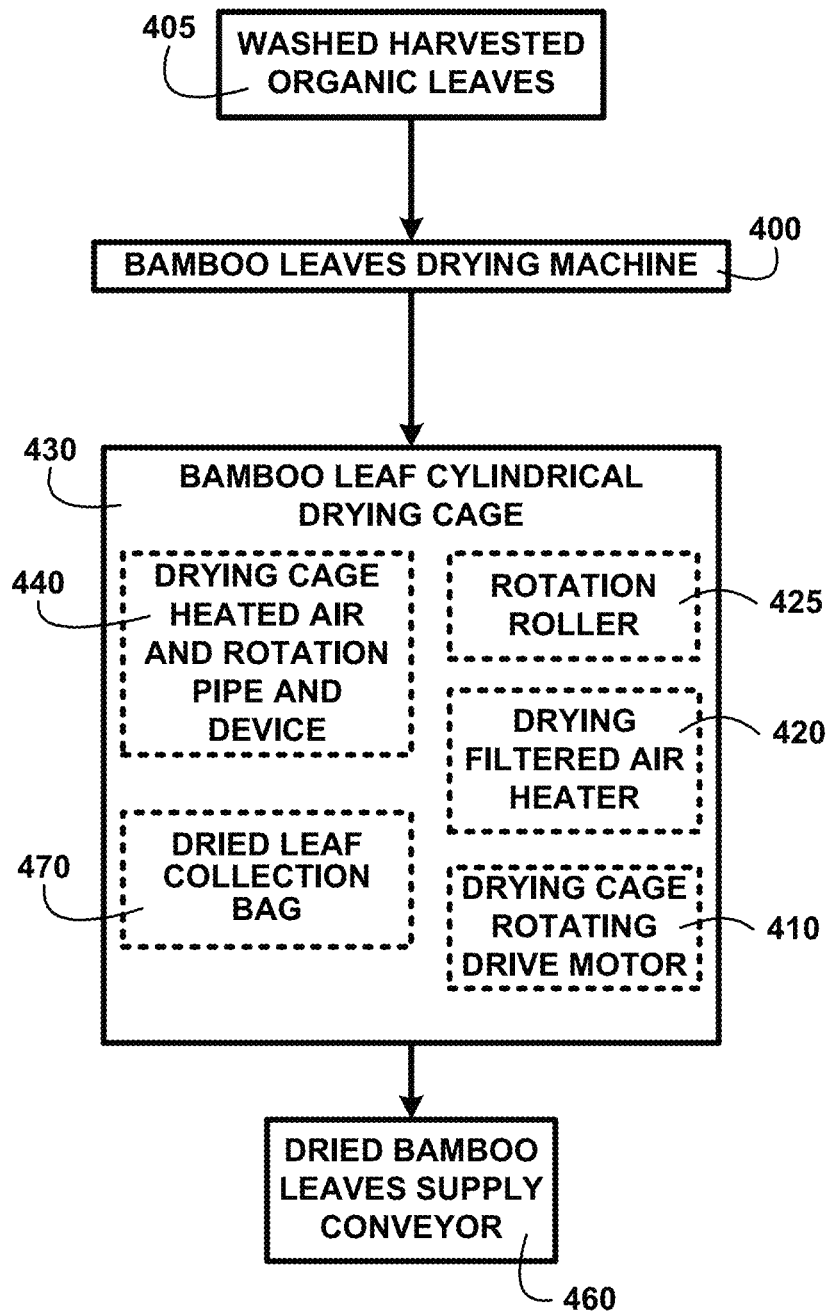
FIG. 4 shows a block diagram of an overview of drying bamboo leaves in a drying machine of one embodiment.

Bamboo Leaves Drying Machine:

FIG. 4 shows a block diagram of an overview of bamboo leaves drying machine of one embodiment. FIG. 4 shows the washed harvested organic leaves 405 conveying of freshly harvested and washed harvested organic leaves 405 for placement in a bamboo leaves drying machine 400. The bamboo leaves drying machine 400 is using hot air to sterilize and dry the washed harvested organic leaves 405. A bamboo leaf cylindrical drying cage 430 includes a drying cage rotating drive motor 410 that provides the force for rotating the bamboo leaf cylindrical drying cage 430. Rotating the bamboo leaf cylindrical drying cage 430 on rotation roller 425 devices tumbles the bamboo leaves to separate leaves from one another and allow the heated air to contact each of the leaves. A drying filtered air heater 420 generates the sterilizing hot air at predetermined temperatures to kill any microbial organisms present on the bamboo leaves which are fed into the bamboo leaf cylindrical drying cage 430 through a drying cage heated air and rotation pipe and device 440. The sterilized and dried bamboo leaves are then conveyed on a dried bamboo leaves supply conveyor 460 into a bamboo leaf shredder of one embodiment.

Figure 5:
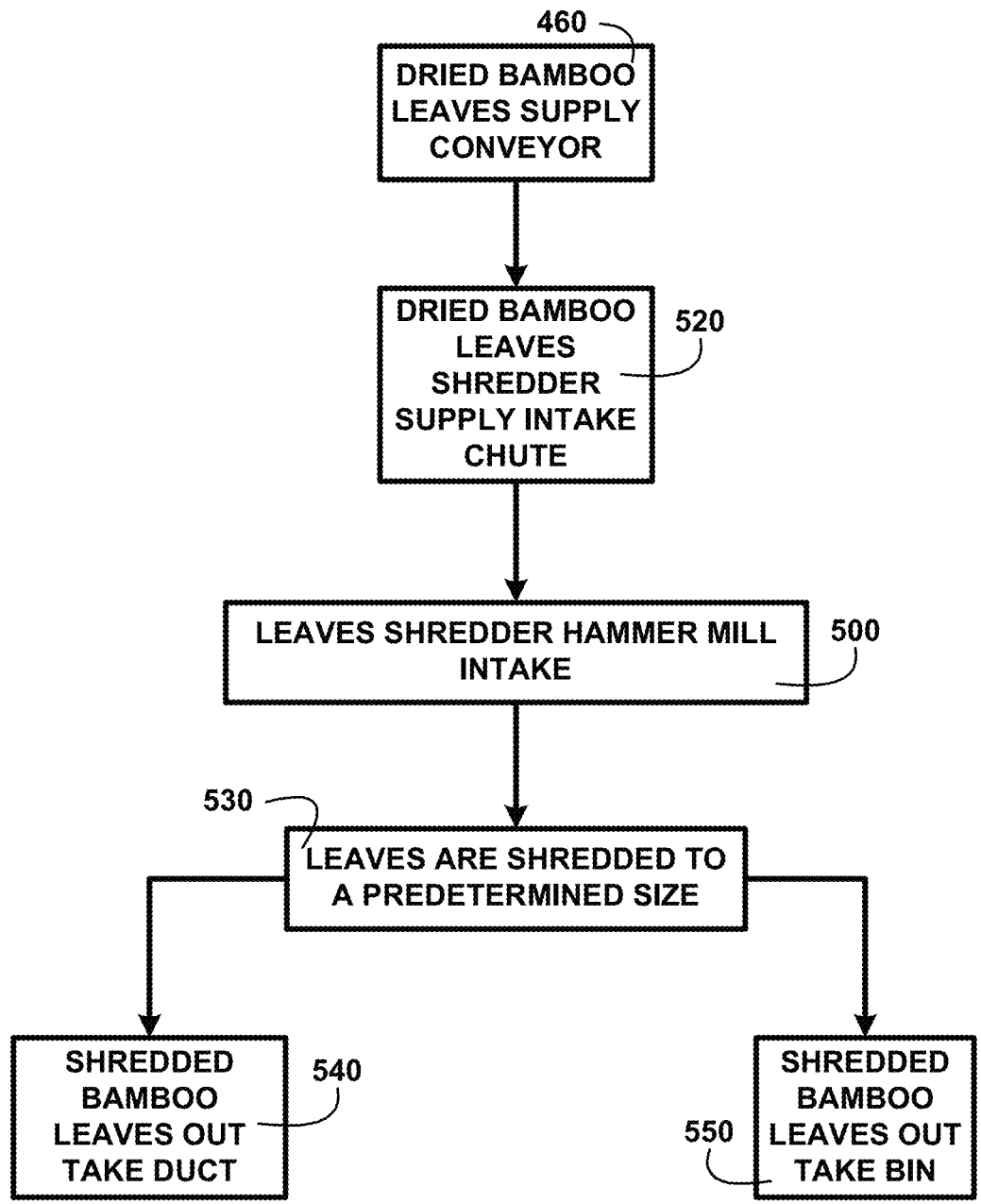
FIG. 5 shows a block diagram of an overview of shedding bamboo leaves using a shredder hammer mill of one embodiment.

Leaves Shredder Hammer Mill Intake View:

FIG. 5 shows a block diagram of an overview leaves shredder hammer mill intake view of one embodiment. FIG. 5 shows the dried bamboo leaves supply conveyor 460 conveying the dried bamboo leaves to a dried bamboo leaves shredder supply intake chute 520. When deposited into a leaves shredder hammer mill intake 500 leaves are shredded to a predetermined size 530. Shredding the dried bamboo leaf facilitates extraction of the essences of the bamboo leaf properties components of one embodiment. After the shredding operation is complete the shredded bamboo leaf materials are removed and conveyed to a shredded bamboo leaves out take duct 540 where the shredded bamboo leaf materials are collected in one or more shredded bamboo leaves out take bin 550 for movement to the next process step. The shredded bamboo leaves out take duct 540 can also be redirected for a direct feed to an extraction machine of one embodiment.

Figure 6:
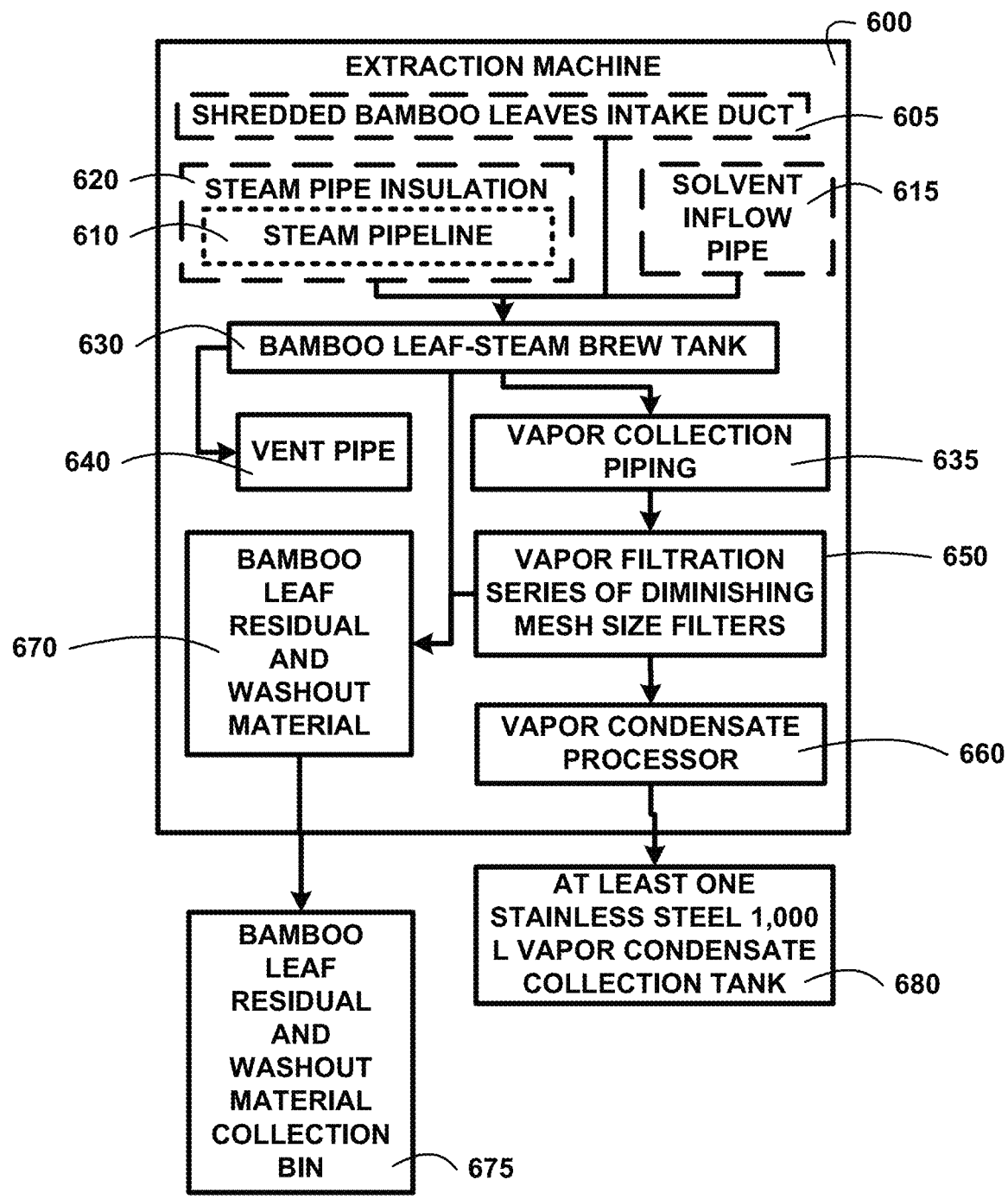
FIG. 6 shows a block diagram of an overview of an extraction machine of one embodiment.

Extraction Machine:

FIG. 6 shows a block diagram of an overview of extraction machine of one embodiment. FIG. 6 shows an extraction machine 600 used for extracting the essences of the shredded bamboo leaf materials properties components. A sterilized water steam pipeline 610 with steam pipe insulation 620 to maintain a predetermined temperature conveys the sterilized water steam to a series of bamboo leaf-sterilized water steam brew tank 630 devices with a supply of the shredded bamboo leaf materials. A solvent inflow pipe 615 delivers a solvent that is used to further facilitate the extraction process. Inside the bamboo leaf-sterilized water steam brew tank 630 unit the sterilized water steam causes the evaporation of the shredded bamboo leaf materials into a vapor. A vent pipe 640 prevents over pressure conditions. The vapor passes through vapor collection piping 635 to a vapor filtration series of diminishing mesh size filters 650 to remove particulate suspended in the vapor. A vapor collection piping 635 system transports the filtered sterilized water steam with evaporated bamboo leaf properties components to a vapor condensate processor 660. The vapor condensate processor 660 condenses the vapor into a liquid which is collected in a condensate form and conveyed to at least one stainless steel 1,000 l vapor condensate collection tank 680

Periodically a device closes the intake valve and flushes the bamboo leaf-sterilized water steam brew tank 630 to remove the bamboo leaf residual and washout material 670. At the same time the vapor filtration series of diminishing mesh size filters 650 is flushed to remove any captured particulates. The bamboo leaf residual and washout material 670 is collected in a bamboo leaf residual and washout material collection bin 675 which strains any liquid and sends it to a water reclamation apparatus of one embodiment.

Figure 7:
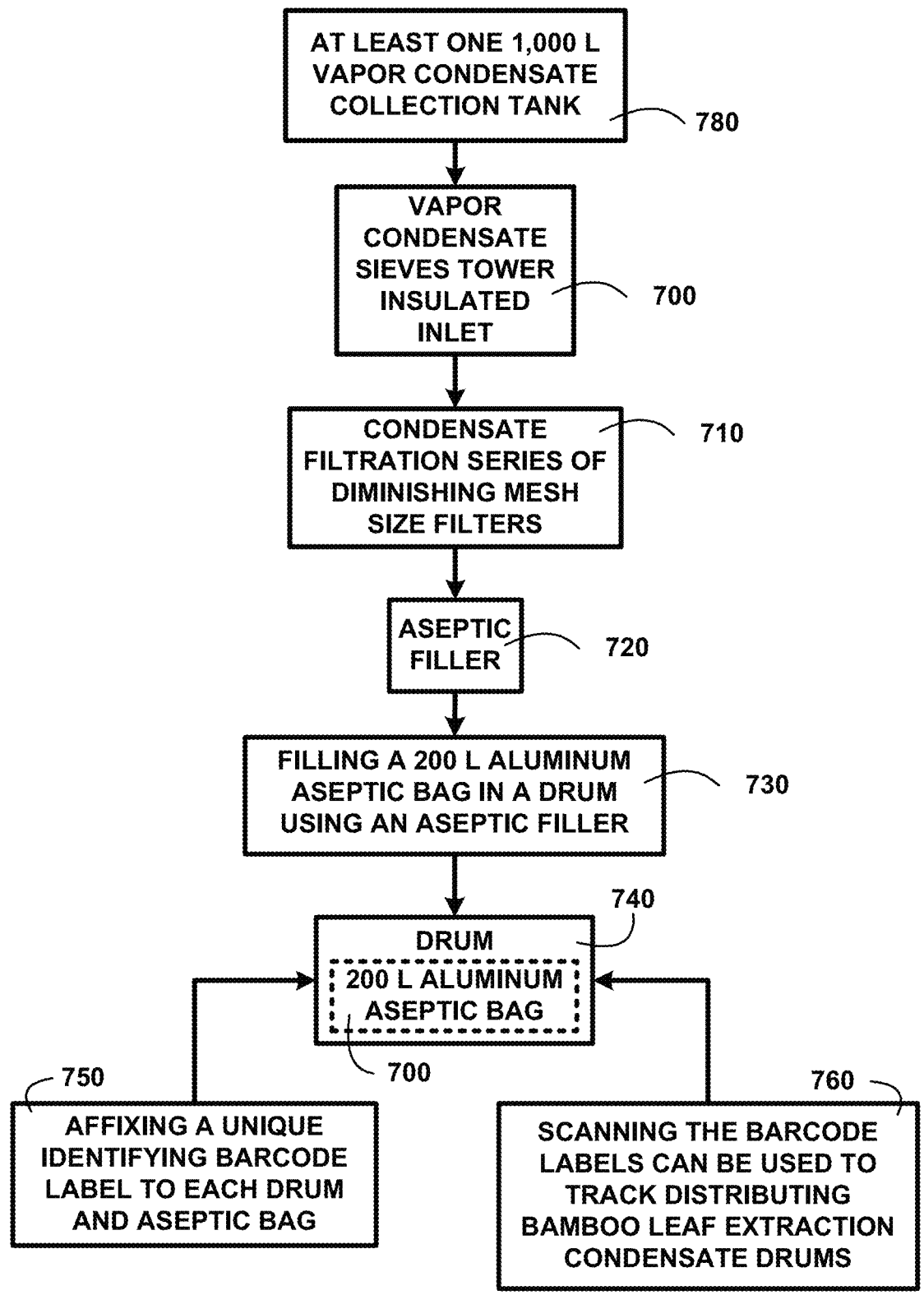
FIG. 7 shows a block diagram of an overview of an aseptic filler of one embodiment.

Aseptic Filler:

FIG. 7 shows a block diagram of an overview of aseptic filler of one embodiment. FIG. 7 shows filling a 200 l aluminum aseptic bag in a drum using an aseptic filler 700. The aseptic filler 710 is conveying the bamboo leaf extract condensate into a 200 l aluminum aseptic bag 720 placed in a metal drum 730. The bamboo leaf extract condensate contained in the aseptic bag within the sealed metal drum 730 can then be shipped to remote locations for bamboo leaf extract processing into final bamboo leaf extract based products. Affixing a unique identifying barcode label to each drum and aseptic bag 750. Scanning the barcode labels can be used to track distributing bamboo leaf extraction condensate drums 760 of one embodiment.

Figure 8:
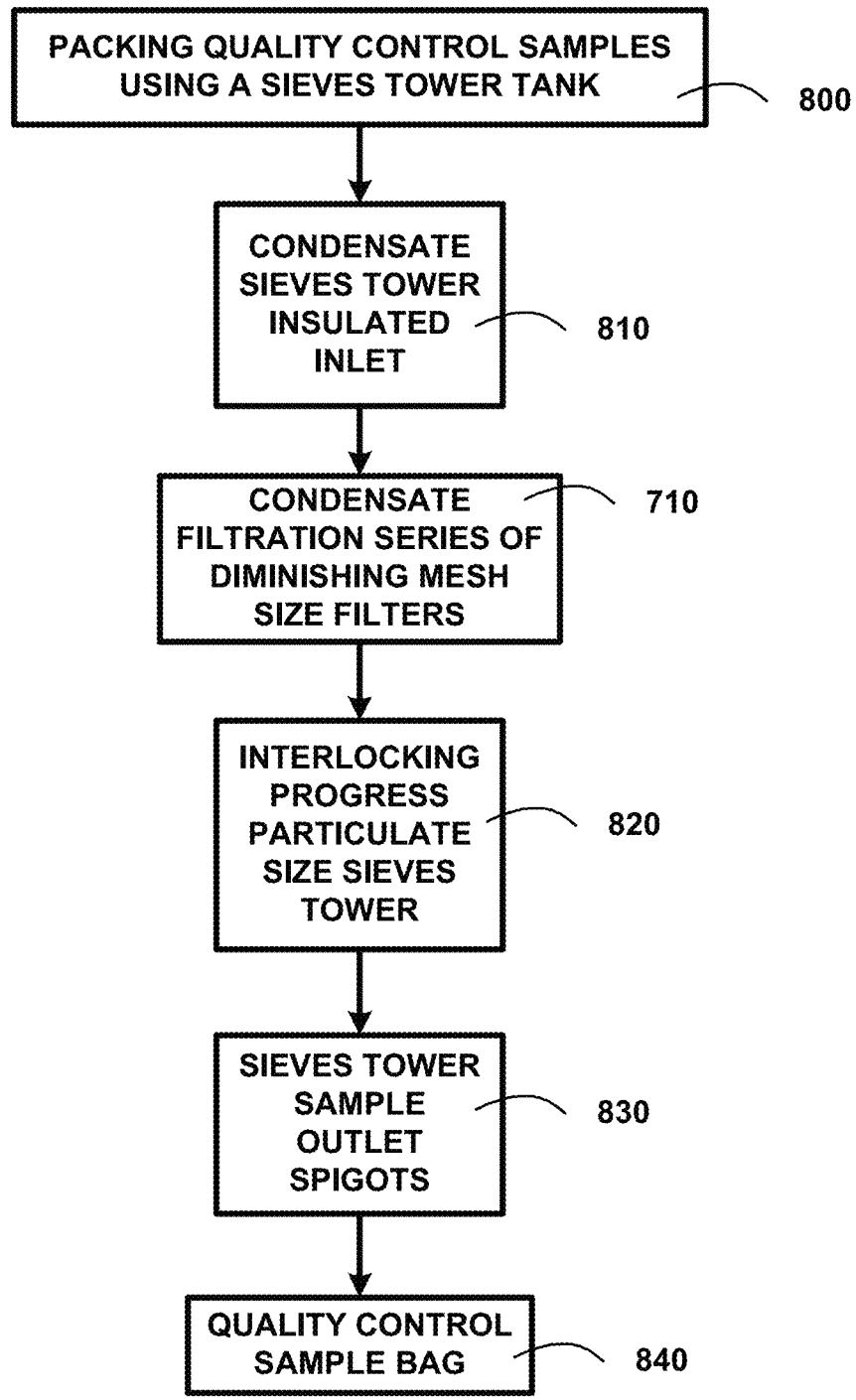
FIG. 8 shows a block diagram of an overview of packing quality control samples using a sieves tower tank of one embodiment.

Packing Quality Control Samples Using a Sieves Tower Tank:

FIG. 8 shows a block diagram of an overview of packing quality control samples using a sieves tower tank of one embodiment. FIG. 8 shows packing quality control samples using a sieves tower tank 800. A vapor condensate sieves tower insulated inlet 830 delivers a sample portion of the bamboo leaf extract condensate to the intake of a sieves tower 810. The condensate filtration series of diminishing mesh size filters 710 progressively removes ever finer particulates of the bamboo leaf pulp. The sieves tower 810 includes multiple progressively finer sieves for filtering the particulates from the bamboo leaf extract condensate. Samples of the filtered bamboo leaf extract condensate are collected in a quality control sample bag 820 for transport to the inspection area of one embodiment.

Figure 9:
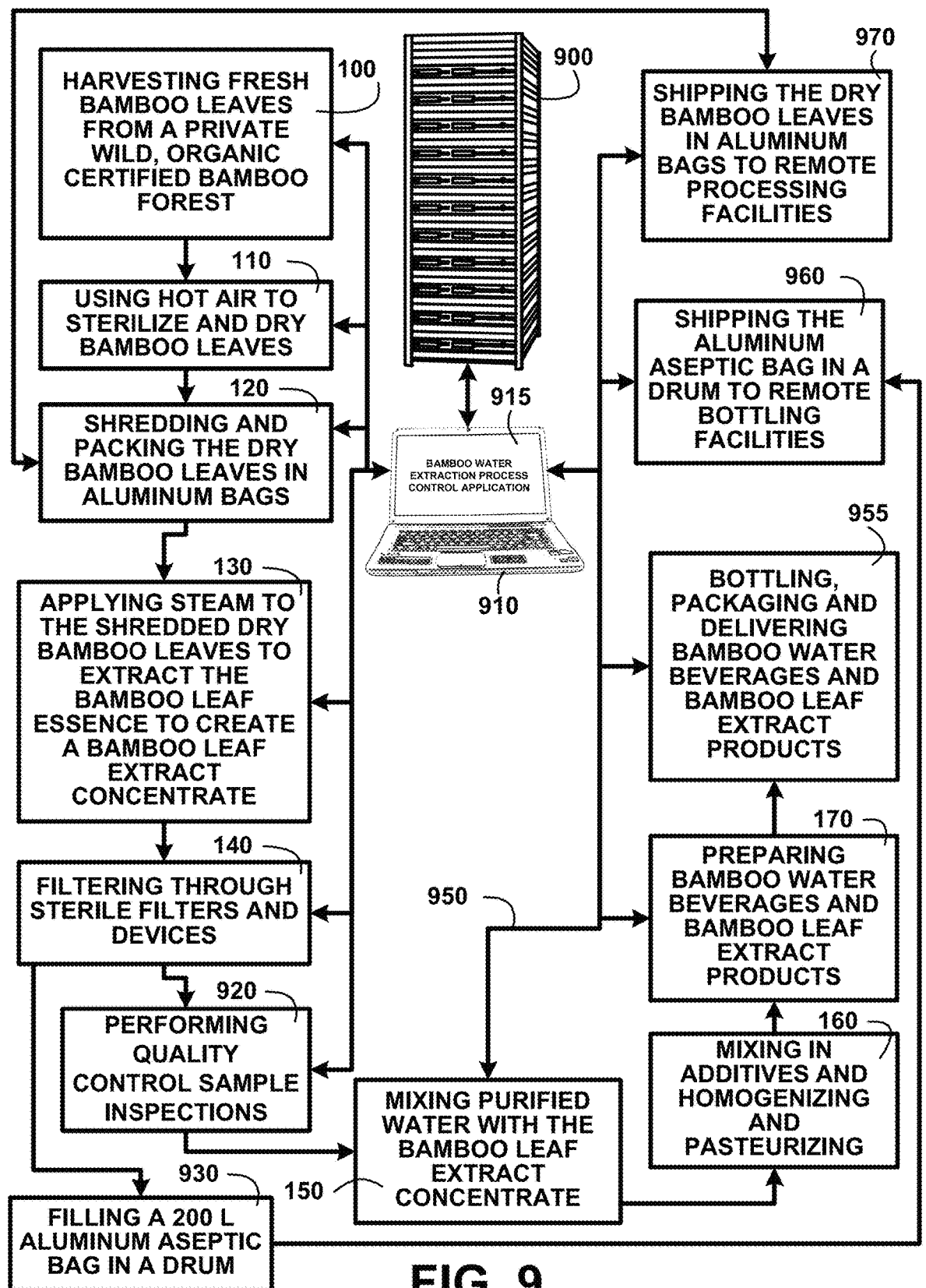
FIG. 9 shows a block diagram of an overview of a bamboo leaf process flow of one embodiment.

Bamboo Leaf Process Flow:

FIG. 9 shows a block diagram of an overview of bamboo leaf process flow of one embodiment. FIG. 9 shows a bamboo leaf extraction network server 900 coupled to a bamboo leaf extraction network computer 910 with a bamboo water extraction process control application 915. The predetermined processing steps are entered into the bamboo leaf extraction network computer 910 and stored on the bamboo leaf extraction network server 900. At least one digital processor controller is coupled to the process devices. The at least one digital processor controllers include digital sensors to measure process conditions for example temperature and pressure and transmit continuously this data to the bamboo leaf extraction network server 900. Adjustments to the devices operating controls settings can be made to maintain the predetermined process step conditions.

The harvesting fresh bamboo leaves from a private wild, organic certified bamboo forest 100 of FIG. 1 culminated in the delivery of the harvested fresh bamboo leaves. An automated digital scale is used to weigh the deliveries and transmits the quantity weights to the server. The speed of rotation and temperature of the heated air are measured using sensors to maintain proper conditions during drying harvested bamboo leaves. Performing quality control sample inspections 920. An automated conveyor system can be used for depositing dried bamboo leaves for shredding and removing shredded bamboo leaves. The duration of the shredding operation can be measured and reported using digital sensors. Filling a 200 l aluminum aseptic bag in a drum 930.

Figure 10:
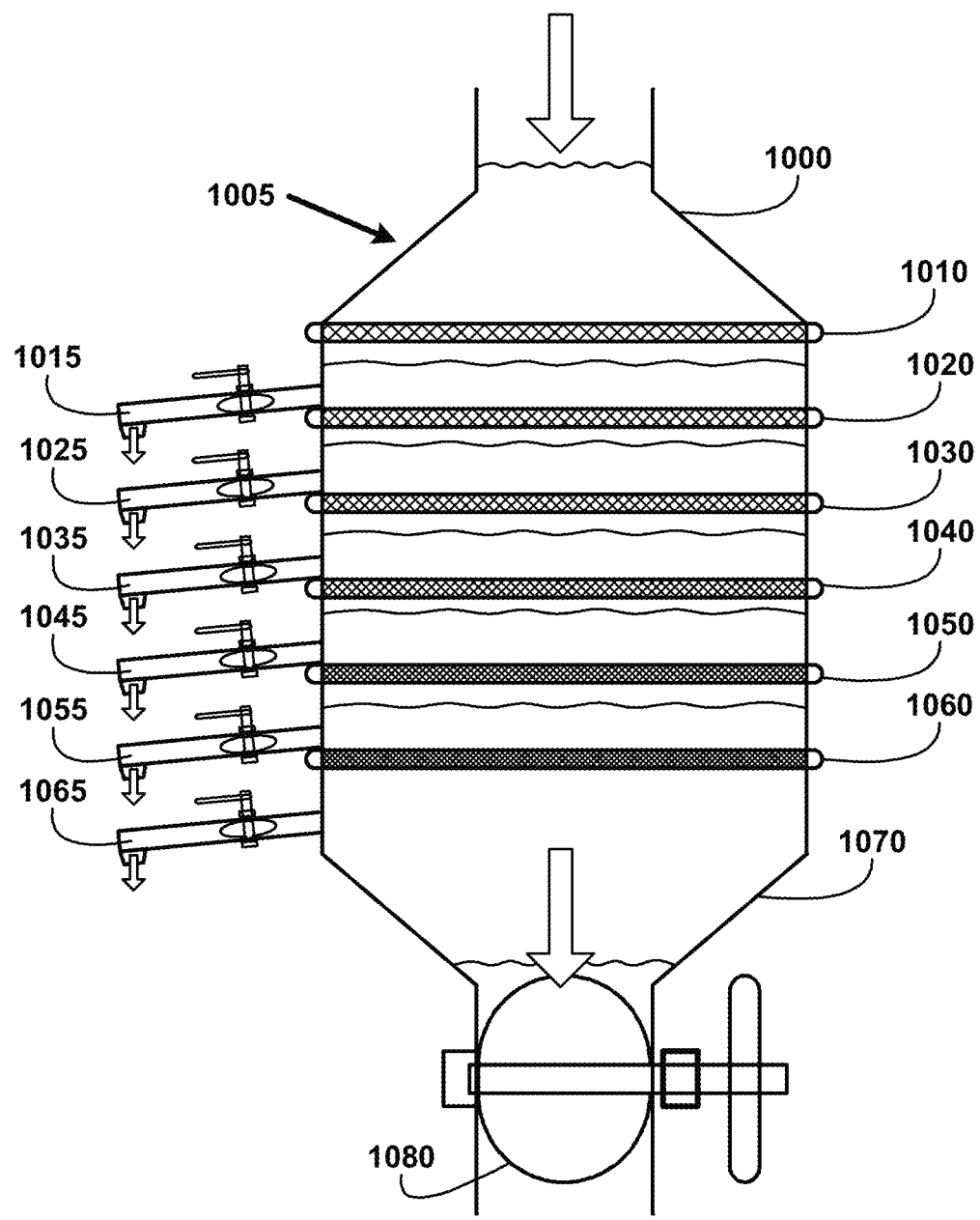
FIG. 10 shows for illustrative purposes only an example of a sieves tower of one embodiment.

At least one digital sensor and corresponding controller can be used for extracting the essence of bamboo from shredded bamboo leaves 950 wherein the at least one digital sensor and corresponding controller can maintain and adjust extraction temperatures and steam to optimize the extraction process. The conveyance of bamboo leaf extract condensate samples can be controlled using the bamboo leaf extraction network server 900 to open and close digitally controlled valves in accordance with quality control inspection schedules entered into the bamboo leaf extraction network computer 910 for packing quality control samples using a sieves tower tank. Server controlled pumps and valves can be used for collecting bamboo leaf vapor condensate in a tank 960 and measure quantities being collected into the tanks. Automated valves can be opened and closed to dispense a predetermined quantity of the bamboo leaf vapor condensate for filling 200 l aluminum aseptic bag in a drum using an aseptic filler 730 of FIG. 7. Affixing a unique identifying barcode label to each drum and aseptic bag 750 of FIG. 7. Scanning the barcode labels can be used to track distributing bamboo leaf extraction condensate drums 760 of FIG. 7. Shipping the aluminum aseptic bag in a drum to remote bottling facilities 960. Shipping the dry bamboo leaves in aluminum bags to remote processing facilities 970. BOTTLING, PACKAGING AND DELIVERING bamboo water beverages and bamboo leaf extract products 955 of one embodiment Sieves Tower:

FIG. 10 shows for illustrative purposes only an example of sieves tower of one embodiment. FIG. 10 shows the sieves tower 1005 with a bamboo leaf extraction condensate intake 1000. The sieves tower 1005 progressive finer sieves includes a #1 sieve filter mesh 1010 with a #1 sieve filter mesh quality control outlet 1015, #2 sieve filter mesh 1020 with a #2 sieve filter mesh quality control outlet 1025, #3 sieve filter mesh 1030 with a #3 sieve filter mesh quality control outlet 1035, #4 sieve filter mesh 1040 with a #4 sieve filter mesh quality control outlet 1045, #5 sieve filter mesh 1050 with a #5 sieve filter mesh quality control outlet 1055, and #6 sieve filter mesh 1060 with a #6 sieve filter mesh quality control outlet 1065 where samples are collected at each filter level. A bamboo leaf extraction condensate sieve collection chamber 1070 accumulates the filtered condensate for a bamboo leaf extraction condensate outtake 1080 from which the condensate is pumped into the condensate collection tanks of one embodiment.

Bottled Bamboo Water:

FIG. 11A shows for illustrative purposes only an example of bottled bamboo water of one embodiment. FIG. 11A shows a bamboo water bottle 1100 used in a bottling process for the various bamboo water beverages. A bamboo water label 1110 identifies the bamboo water based beverage filled into the bottle. A bamboo water ingredient label 1120 identifies the ingredients including the bamboo water and any additives used in the mixture filled into the bamboo water bottle 1100 of one embodiment.

Bamboo Leaf Tea Bag:

FIG. 11B shows for illustrative purposes only an example of bamboo leaf tea bag of one embodiment. FIG. 11B shows a tea bag 1130 filled with dried shredded bamboo leaf 1131. Coupled to the tea bag 1130 is a label coupling string 1132 coupled to a label 1133. The label 1133 is a bamboo leaf tea product label 1134 identifying an organic bamboo leaf tea ingredient 1135 of one embodiment.

Bamboo Tea Beverage:

FIG. 11C shows for illustrative purposes only an example of bamboo tea beverage of one embodiment. FIG. 11C shows a tea cup 1140 with the tea bag 1130 with the bamboo leaf tea product label 1134 showing the organic bamboo leaf tea ingredient 1135. The tea bag 1130 is shown immersed in hot water for preparing a bamboo leaf tea steeping in a tea cup 1150 in one embodiment.

Figure 12:
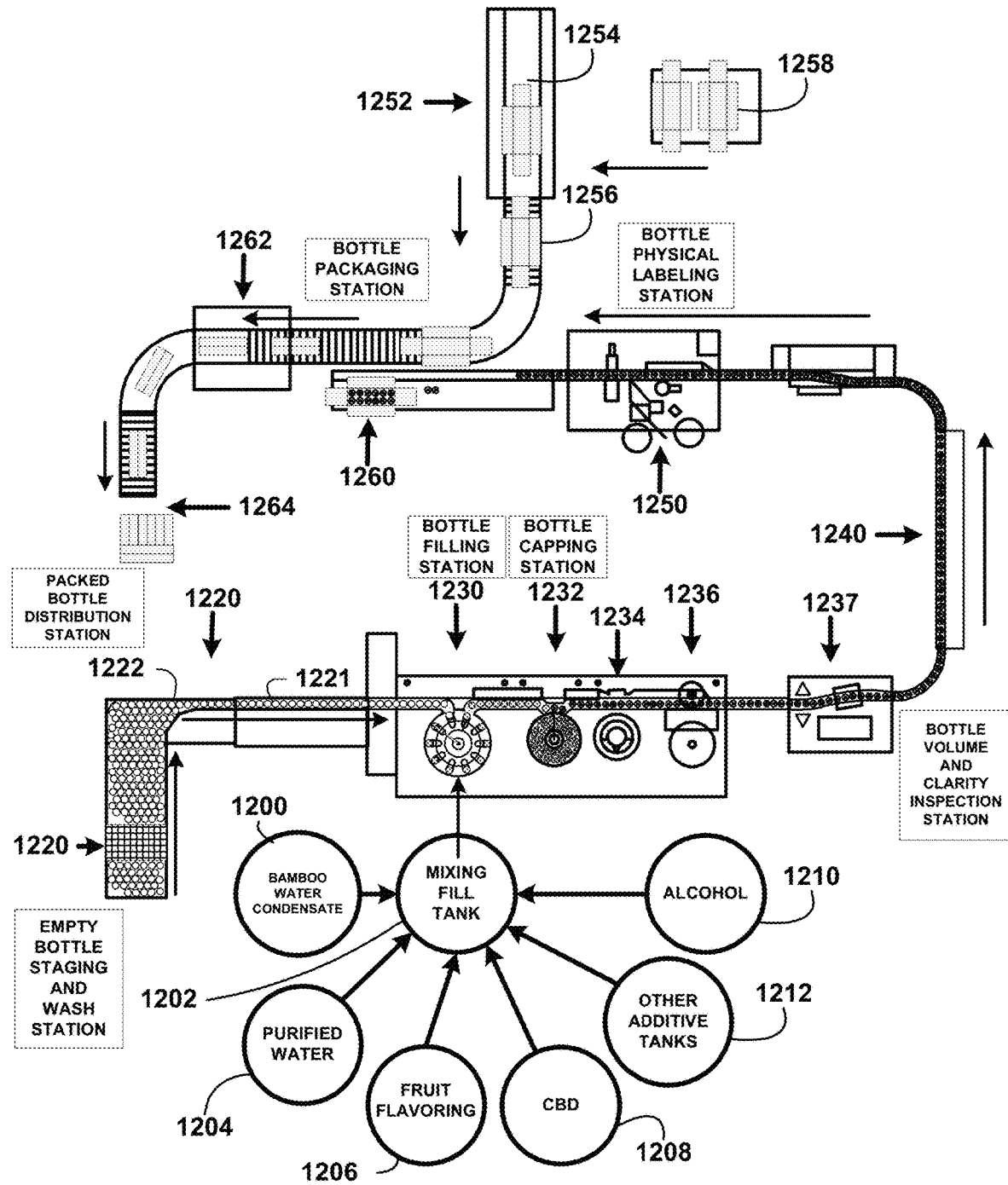
FIG. 12 shows for illustrative purposes only an example of a bamboo leaf extract beverage bottling process of one embodiment.

Bamboo Leaf Extract Beverage Bottling Process:

FIG. 12 shows for illustrative purposes only an example of bamboo leaf extract beverage bottling process of one embodiment. FIG. 12 shows an empty bottle staging and wash station 1220. The staged and washed empty bottles are directed to an empty bottle alignment channel 1222 and conveyed on a single row empty bottle conveyor 1221 to a bottle filling station 1230. A bamboo water condensate tank 1200 is controlled to deposit bamboo water condensate into a mixing fill tank 1202 where a purified water tank 1204 mixes in a predetermined volume of purified water. The mixture may include other additives that will be deposited from a fruit flavoring tank 1206, CBD tank 1208 for hemp and medicinal legalized CBD and medicinal legalized cannabis ingredients, or alcohol tank 1210 for alcohol neutral spirits or distilled alcohol and whisky, beer, wine, and/or other additives tanks 1212 for other additives and ingredients including those shown in FIG. 12 according to a predetermined formulation. The empty bottles are filled from the mixing fill tank 1202 with a predetermined volume.

The filled bottles are conveyed to a bottle capping station 1232 to affix a cap on the bottle. A first bottle printed labeling station 1234 can print a product name on the bottle. A second bottle printed labeling station 1236 can print product ingredients on the bottle. Bamboo extract alcoholic beverages include bottling labeling and packaging processes and devices configured for printing and checking preprinted beverage container labels and packing content labeling inspection to assure required information including a text and an alphanumeric code and graphic barcode that includes a unit package production code, kind of product, beverage container type and size, ABV quantity and proof of the spirits, Alcoholic Beverage Health Warning Statement are accurate and included.

A bottle volume and clarity inspection station 1237 uses a digital scale to measure the weight of the filled bottle and using a laser and camera check the color and clarity of the beverage liquid. A bottle inspection station 1240 is where a human inspector can check that the bottles are properly capped and labeled. A bottle physical labeling station 1250 can affix for example a barcode label to the bottle. A packaging labeling station 1258 can print the product information and data to the packaging materials. A packaging assembly station 1252 and box preparation station 1254 is used to prepare the packaging for bottle insertion.

A packing conveyor 1256 delivers the packing materials to a bottle packaging station 1260. In one embodiment a robotic device can pick-up and place bottles into for example a packaging box. A packaging sealing station 1262 closes the packaging and seals it for distribution. A packed bottle distribution station 1264 in one embodiment can use a robotic device for conveying for example packed boxed for placement on a palette for distribution conveying of one embodiment.

Bamboo Water Bottling Process:

In the following description the terms "bottle" and "bottling" have the meaning of a "beverage container" including a glass bottle, a can including an aluminum can, a food grade plastic bottle, a food grade beverage container that is biodegradable, a beverage container made with an ultraviolet protective tinting or exterior coating, and wherein each type of beverage container may be of any volume capacity. The beverage container can include an opening device including a "pop top" opening device, a screw-on cap made of a food grade plastic or aluminum, a crimped cap, a cork, a sealed detection device and other types of capping devices.

A bamboo water bottling process begins with an empty bottle supply bin where empty bottles are positioned for processing through an empty bottle conveyor alignment apparatus. The empty bottles are fed in a single row onto a single empty bottle conveyor. The process includes a de-ionized purified water empty bottle sanitation station where the bottles are rinsed clean in a bottle cleaning area. The sanitizing rinse includes de-ionized purified water from an empty bottle sanitation station de-ionized purified water supply tank and can include heating the de-ionized purified water to a temperature ranging from 110° F. to 180° F. The elevated temperature and de-ionization of the purified water sanitizes the bottle and removes minerals that could remain on the surfaces of the bottles. The minerals that are removed may be some of the same minerals being added later in the processing, but the amount of the minerals in the purified water rinsing cycle may be unknown and may cause a quantity of mineral in the final beverage formulation greater than a predetermined amount to be added. The rinse water used is recycled to the treating water processes.

All bottling facilities shall apply for and retain on file in the bottling facilities current certificates or notifications of approval issued by the government agency or agencies approving the plant's source and supply of product water and operations water. All required certificates or notifications of approval shall be available for review at reasonable times. Bottling facilities can include for example an empty bottle filling station room with tight walls, ceilings, and self-closing doors not shown separate from other bottling operations with double self-closing passage doors that cannot open directly into any room for protection against contamination. Conveyor openings are sized to permit passage of containers. Processing operations can include a sealed system under internal air pressure to prevent infiltration of outside air that may contain particulates and microbial organisms and adequate protection to preclude contamination of the water and the processing system. Adequate ventilation is included to minimize condensation in processing rooms, bottling rooms, and in a bottle cleaning area for washing and sanitizing bottles.

The bottle cleaning area can include an enclosed room, not shown, for preventing post-sanitizing contamination of the bottles. The empty bottle filling station can include a sealed room not shown that includes double passage doors to prevent contamination from outside air. All double passage door passage ways will include positive air pressure to prevent infiltration of outside air and floor vacuum exhaust apparatus to remove soil, dust and other clothing contaminates possibly on personnel clothing. The floors will include footwear brushing apparatus to permit personnel to brush off any debris on the soles of their footwear. The turbulent positive air pressure blowers will include ultrafiltration and sufficient turbulence to knock lose any particulates on their clothing. Positive air pressure shall be free of oil, dust, rust, excessive moisture, and extraneous materials and shall not affect the bacteriological quality of the water and should not adversely affect the flavor, color, or odor of the water.

All product water and operations water supplies are properly located, protected, and operated, easily accessible, adequate, and of a safe, sanitary quality compliant at all times with the applicable laws and regulations of the government agency or agencies having jurisdiction. Finished bottled water must comply with bottled water quality standards.

Bottling facilities can include locker and lunchrooms that are separate from plant operations and storage areas and include self-closing doors. Procedures will be established to maintain locker and lunchrooms in a clean and sanitary condition with refuse containers should be provided. Bottling materials and supplies will not be stored in locker or lunchrooms.

Next the empty bottles are processed through an empty bottle air cleaner station. The filtered compressed air is injected into the empty bottles from an empty bottle air cleaner station compressed air supply tank. This dries the empty bottles and prevents any particulates from the air from remaining in the empty bottles. Bottles are then conveyed into an empty bottle filling station.

The bamboo water bottling process includes but is not shown at least one test valve at each supply piping coupled to a supply tank for taking samples of for example waters, liquids and powders. The samples taken are used for testing of microbial and non-organic substances at least weekly. Microbial testing includes for example heterotrophic plate count, coliforms, mold, yeast, *Pseudomonas aeruginosa*, bacteria, protozoa, fungi, viruses, *E. coli*, and other microorganisms and bacteria. The samples are taken at a predetermined periodic basis. If any coliform organisms are detected, follow-up testing must be conducted to determine whether any of the coliform organisms are *E. coli*. Sample test results reports are logged into the bamboo water bottling process server including date of sampling, type of product sampled, unit package production code, and results of the analysis and reported to appropriate agencies. While samples are tested in approved laboratories there are also on-site automated testing devices to preform immediate preliminary test results. The on-site automated testing devices are activated by a bamboo water bottling process server signal to each testing device to open the at least one testing valve using a solenoid and process the sample through the on-site automated testing device for detecting microbial and non-organic substances.

Should the preliminary test results indicate the presence of a targeted microbial organism the on-site automated testing devices transmit an alert signal to activate a pulsing red light at the location of the at least one test valve, activates an audio alarm and activate a shut-down of the additive supply valve to prevent contamination beyond that point. The automated testing devices transmitted alert signal and test results also is received by a bamboo water bottling process server which relays the signal over a WI-FI communication device to supervisory and management personnel using texting, email and a recorded alert message over a voice communication.

Other on-site automated testing devices automatically test a sample for targeted non-organic substances including for example minerals, bamboo leaf extract quantities, a heavy metal assay, arsenic, uranium, antimony, beryllium, cyanide, nickel, thallium, diquat, endothall, glyphosate, dioxin, phosphorus, phosphates, sodium carbonate, sodium bicarbonate, potassium bicarbonate, calcium carbonate, calcium-magnesium carbonate, potassium hydroxide, sodium hydroxide, phosphoric acid, acetic acid, citric acid, hydrochloric acid and sulfuric acid, residual disinfectants and disinfection byproducts, and chemical pesticides. On-site automated testing devices ample test results reports are logged into bamboo water bottling process server including date of sampling, type of product sampled, unit package production code, and results of the analysis and reported to appropriate agencies.

The empty bottle filling station is supplied with a beverage mixture from a beverage mixing tank for filling the beverage mixture into the bottles in a predetermined volume. Predetermined amounts of ingredients are combined and mixed in the beverage mixing tank. The ingredients can include predetermined quantities of purified water from a tank, and bamboo leaf extract, and bamboo leaf extract additives. The beverage mixture can also include in predetermined quantities flavorings, additives, vitamins, minerals, carbonation, one or more artificial sweetener, and one or more natural sweetener. The total predetermined quantities of the ingredients are deposited into the beverage mixing tank and blended into the final product mixture. Bottle filling can include a number of technologies that can be used based on the beverage mixture, type of beverage container and other factors of one embodiment.

Hot Fill:

The bottle filling process includes at least one sterilization process. The at least one sterilization process includes a hot fill process. The hot fill apparatus includes heating elements along the metal fill piping. The beverage containers are moved along the conveyor to an adjustable platform. The adjustable platform is automatically adjusted up or down to a fill height determined by a laser sensor that detects the top of the container. A digitally controlled valve of the heated metal fill piping is opened and closed using a signal from the bamboo leaf extraction network computer to dispense a predetermined volume of the heated mixed liquid that will fill the container to a predetermined volume below the top of the container.

The hot fill process heats the mixed liquids between 194 and 203 degrees Fahrenheit to ensure sterilization. These heat-up process temperatures can be used with glass and certain types of plastic containers that do not change form at these temperatures. The containers are filled with the heated mixed liquids including non-carbonated beverage and liquid food products such as fruit and vegetable juices, soft drinks, water and teas. The containers are hermetically sealed after filling to preserve the sterilization. The hermetically sealed containers are immediately cooled preserving the product and taste. The hot filling process eliminates the need of preservatives and chemicals while maintaining the same level of shelf life and nutritional properties of the beverage.

Cold Fill:

The at least one sterilization process includes in another embodiment a cold fill process. The cold fill process pressurizes the container by cooling the product then the cold product is added to the cold container. The cold fill process requires sterilization, which can be either a wet or dry sterilization. The cold fill process includes at least one of three cold fill technologies.

A first cold fill technology is Iso-barometric Fillers: Applied to carbonated soft drinks, where the packaging, in PET plastic or glass is filled in iso-barometric fillers, capped and pasteurized in an Iso-barometric tunnel. Filling is made at 3° C. to 4° C. temperatures.

A second cold fill technology is Ultra Clean Systems: applied to beverages filling at low temperatures, and where the environmental conditions are very strict. This type of cold fill process is used or products with a short expiring date of about 30 days—and are distributed at low temperature under chilled conditions. The products have high quality, and are flash pasteurized and including a flash pasteurized application to the carton and PET packaging.

A third cold fill technology is Steril filling: Sterile filling preserves the product best according to nutritional, organoleptic and shelf life qualities. Sterile filling processing sterilized the container before filling in a sterile environment, sterilizing the container with peroxide or per-acetic acid, then dried to eliminate any traces of it. The sterility of the filling atmosphere is achieved via air filtering and high temperature sterilization. Sterile filling can be used for carton packaging containers and PET bottles.

Aseptic Fill:

The at least one sterilization process includes in another embodiment Aseptic fill. The aseptic filling process flash pasteurizes the mixed product including the mixed liquid is heated to a temperature between 180° F.-220° F. for a few minutes then cooled and filled at room temperature. Aseptic processing is a process by which a sterile product including at least a food or pharmaceutical, is packaged in a container. Aseptic fill is appropriate for high acid products and the products can last up to 18 months and is great for dairy and beverages in glass, aluminum, or PET.

Mixing Tanks:

Mixing tanks, sometimes called Blending tanks can include single direction rotating paddles, counter-rotating paddles, multi-speed rotating dual blades and combination homogenizing mixing tanks.

Filtration:

Filtration is integrated along the flow lines of the liquids at every point where the liquid is being conveyed from one vessel to another. For example when a liquid is pumped from a storage tank to the mixing tank a series of filters of various mesh sizes are incorporated into the piping lines. At least one filter in the series of mesh sizes is 0.2 microns to capture bacteria. Multiple filtration assures clean clear beverages.

After the bottles are filled at the empty bottle filling station they are conveyed to a bottle capping station where a cap is coupled to the filled bottle. A bottle volume sensor station then is used to confirm the predetermined volume has been filled into the bottle. A bottle labeling station then affixes a label to the bottle. In some instances the bottle or beverage container may be pre-printed with the labeling information including the product name, contents information and other desired and required information.

The bottles are conveyed to a bottle quality control station where one or more inspector and/or automated sensors including scanners, photographic image recognition devices, digital scales and other quality control evaluation test devices can perform quality control inspections to ensure the quality of the bottling processes. The bottles that pass the bottle quality control station evaluations are then conveyed to a bottle packing station. During the process of filling, capping or sealing either single-service or multiservice containers, the performance of the filler, capper or sealer shall be monitored and the filled containers visually or electronically inspected using the automated sensors including scanners, photographic image recognition devices, digital scales and other quality control evaluation test devices to assure they are sound, properly capped or sealed, and coded and labeled. Containers that do not pass inspection shall be reprocessed or rejected and not sent to packaging of one embodiment.

All containers, caps and closures shall be sampled and inspected to ascertain that they are free from microbial organisms and other forms of contamination. Testing for bacteriological contamination shall be performed using approved methods including a bacteriological swab and/or rinse count at least once each 3 months. Testing for bacteriological contamination shall be conducted on not less than four containers, caps and closures selected just prior to filling and sealing. No more than twenty-five percent of the samples may exceed more than one bacterium per milliliter of capacity or one colony per square centimeter of surface area. All samples shall be free of coliform organisms. The procedure and apparatus for these bacteriological tests shall be in conformance with those recognized by the government agency or agencies having jurisdiction. Tests shall be performed either by qualified plant personnel or a competent commercial laboratory.

Predetermined packaging for each beverage type and beverage container is positioned at a bottle packing receiving station. All packaging materials shall be imprinted with a unit package production code. Each unit package from a batch or segment of a continuous production run of bottled drinking water shall be identified by a unit package production code. Imprinting of the unit package production code shall be uniquely codes with unit package production code data including the kind of product, volume produced, date produced, lot code used, and the distribution identification of the finished product to wholesale and retail outlets just prior to packaging of a product. The bamboo water bottling process server shall produce an alphanumeric code and graphic barcode for each finished product batch for each different beverage container type and size. The alphanumeric code and graphic barcode will include codes to distinguish the unit package production code from other batches. The unit package production code shall identify a particular batch or segment of a continuous production run and the day produced. The plant shall record and maintain information as to the kind of product, volume produced, date produced, lot code used, and the distribution of the finished product to wholesale and retail outlets.

Predetermined packaging can include a non-corrosive and non-toxic disinfectant agent impregnated into the packaging materials including for example cardboard and plastic rings to prevent growth of bacteria and microorganisms on the beverage containers after packaging and during shipping. A bottle packing folding station uses the received predetermined packing materials and processes the materials for receiving a predetermined number of bottles. This may include for example folding of packing cartons, drink holders, loading plastic six-pack rings in an application device and other predetermined packing materials preparations. A bottle carton conveyer is used to convey folded cartons to an unloaded carton staging area. The unloaded carton staging area is used for a carton assembly station for packing the cartons with bottles. An assembled carton shipping conveyor is used for grouping and positioning assembled cartons for pick-up for delivery to a shipping area. The above has described an overview of a bamboo water based beverage for human consumption bottling apparatuses and processes of one embodiment.

Computer Controlled Monitoring and Processes:

A bamboo water based beverage for human consumption bottling electronic monitoring and control network used for monitoring and controlling a bottling operation includes at least one digital server, at least one digital processor, at least one digital memory device, at least one Wi-Fi device, at least one database, at least one processing algorithm, and at least one user computer. The at least one digital server controls the bottling processes using data and parameters inputted by a user with the at least one user computer of one embodiment.

User inputted data and additional data is stored in the at least one digital memory device and at least one database creating a reference file for each beverage. The data includes predetermined quantities of each additive ingredient for each beverage to be formulated, a predetermined pH level range for each beverage, a predetermined temperature range, a bottle or beverage container size for a particular packaging mode, labeling information, and detailed information for each additive ingredient including pH level, calories per unit, a sweetness and taste indicator value, and other additive specific data. The at least one processing algorithm includes a formulation process to determine for example a projected pH level based on a combination of specific quantities of additive ingredients. The at least one digital processor is used to calculate the projected pH level based on the volumetric contributions of each additive ingredient of one embodiment.

Additional data is communicated to the at least one digital server using WI-FI communications and data signals from monitoring sensors at various points in the processing. In one embodiment for example, during each process, sensors and tracking devices are connected to each device that processes, mixes, sterilizes, and other operations of the bottles, beverage additive ingredients and bottles to ensure the beginning, intermediate and final processes are controlled to allow the final product to all safety and regulatory standards for human consumption and a desired product quality of one embodiment.

In addition a RFID, Bluetooth, NFC, sensors and tracking devices are coupled to the beverage containers of a beverage product to track the beverage distribution and track the consumption of the beverage product and disposal of the bottle container. A mobile device application is wirelessly coupled to the sensors and devices to allow a user to remotely monitor and observe the distribution, consumption, and disposal of the beverage of one embodiment.

An additive supply tank is equipped to receive an additive quantity control signal from the at least one digital server. The signal is received using a predetermined quantity digital meter and monitor controller transceiver. The additive supply tank includes a plurality of interior facing waterproof ultraviolet light sanitization fixtures to prevent bacterial growth and kill any microorganisms that may be present in the additive material prior to being conveyed to the mixing tank. Coupled to additive bulk supply piping a metered supply pump opens a digitally controlled valve to allow the predetermined quantity to flow to the beverage mixing tank through metered supply piping of one embodiment.

A metered additive temperature control apparatus can receive a metered additive temperature control signal from the at least one digital server using a predetermined digital temperature controller transceiver. Metered additive supply piping is equipped with a digital temperature meter. The digital temperature meter measures the temperature of the additive flow. The digital temperature meter transmits digital instructions through the digital temperature meter thermostat cabling to start the operation of a metered additive supply temperature adjusting apparatus should the additive flow temperature fall below or above a range determined by a predetermined temperature transmitted by the metered additive temperature control signal. The predetermined temperature is set to a range for each specific additive to prevent growth of bacteria in the additive. The metered additive supply temperature adjusting apparatus can operate in a mode to either raise or lower the temperature using a reversible flow of a media in temperature control media piping to extract or add heat to adjust the additive flow temperature of one embodiment.

The beverage mixing tank includes a beverage mixing tank mixer motor. The beverage mixing tank includes a plurality of interior facing waterproof ultraviolet light sanitization fixtures to prevent bacterial growth and kill any microorganisms that may be present in the additive material prior to being conveyed to the mixing tank. An additive ingredient mixing tank control signal is received by the beverage mixing tank using a plurality of pH metering probe and digital transceiver coupled to each metered additive supply piping. At least one pH metering probe and digital transceiver is coupled to purified water supply piping. The pH metering probe and digital transceiver measures the actual pH level of the additive ingredient as it flows into the beverage mixing tank. The actual pH levels are transmitted to the at least one digital server. This actual data is processed by the at least one processing algorithm using the at least one digital processor to determine any pH level adjustment in the combined ingredients of one embodiment.

The purified water supply tank can receive a purified water supply control signal from the at least one digital server using the pH metering probe and digital transceiver. The de-ionized purified water supply control signal can include a final pH level adjustment instruction. The final pH level adjustment instruction is transmitted to a soda ash (NaOH) solution injector apparatus using pH metering probe and digital transmitter signal cabling. The soda ash (NaOH) solution injector apparatus can inject into de-ionized purified water supply piping a predetermined pH level adjustment dose of soda ash to make the adjustment inject that quantity using NaOH injection piping. The de-ionized purified water supply tank includes a plurality of interior facing waterproof ultraviolet light sanitization fixtures to prevent bacterial growth and kill any microorganisms that may be present in the de-ionized purified water prior to being conveyed to the mixing tank of one embodiment.

A bottling conveyor temperature control apparatus is used to control the temperature of the final beverage product after bottling. The bottling conveyor temperature control apparatus surround a section of a bottle conveyor with bottles on a conveyor. The section of a bottle conveyer with the bottling conveyor temperature control apparatus includes in the surrounding structure a plurality of interior facing ultraviolet light fixtures to prevent bacterial growth and kill any microorganisms that may be present on the exterior of the bottles and caps while being conveyed to the bottle packing station.

A bottling conveyor temperature controller transceiver can receive a bottling conveyor temperature control signal with a predetermined temperature. The digital temperature meter can signal using digital temperature meter thermostat cabling the metered additive supply temperature adjusting apparatus to extract or add heat using reversible flow of a media in the temperature control media piping of one embodiment. The bottling electronic monitoring and control network is used for metering, monitoring and controlling combining ingredient quantities, regulating ingredient and mixture temperature and pH level of the mixture of one embodiment.

Bottling Quality Control Process:

Bamboo water bottling quality control processing includes a bottle quality control station. Bottling quality control includes a bottling facility physical plant, sanitation inspection procedures and processes including labeling and packaging. The bamboo water beverage method and system bottling apparatuses and processes includes a bamboo water bottling process server and computer to control and regulate bamboo water bottling quality control processes of one embodiment.

The bottle quality control station processes filled, capped, and sealed bottles for inspections. Qualified personnel conduct physical inspections. Not shown are automated electronic and mechanical sensors and testing devices to inspect for contamination, improper capping and sealing. Inspection results are logged into the bamboo water bottling process server by physical inspectors using the computer. Automated electronic and mechanical sensors and testing devices transmit inspection results to the bamboo water bottling process server. Should a bottle not pass the inspection regimen physical inspectors are alerted by the bamboo water bottling process server of an inspection rejected bottle for physically pulling inspection rejected bottle from the conveyor and transmitting a rejection signal to a robotic gripper for pulling inspection rejected bottle from the conveyor and depositing the inspection rejected bottle in a rejected bottle receptacle of one embodiment.

The bottle packing station is for receiving a unit package production code printing instructions for using a label printer apparatus and label application apparatus to affix a unit package production code includes a barcode and/or a QR code label to a bottle and for direct printing on a bottle surface the unit package production code data to inform consumers of ingredients, nutritional data and other information including a batch identifying code. The unit package production code barcode and/or QR code is read for example using an application on a users' smart phone of one embodiment.

Non-corrosive and non-toxic disinfectant agent impregnated flattened packaging materials are positioned for using a printer to print a unit package production code. The unit package production code including a barcode and/or a QR code on the flattened packaging materials are for providing automated identification of product batch data and packaged product tracking. Flattened packaging with a printed barcode passes through a barcode reader scanner with QR code reading capability to track the numbers of batch indicated product packaging used for a particular batch. The flattened packaging with a printed barcode is conveyed to the bottle packing receiving station for processing through the bottle packing folding station. Folded bottle packing materials are set on the bottle carton conveyer for movement to the unloaded carton staging area of one embodiment.

The carton assembly station includes automated processes for robotic (not shown) placing of inspection approved filled, capped and sealed bottles in folded carton packaging. Folded packaging with bottles packed inside is processed to complete sealing of closed packaging with a plurality of labeled bottles. Another barcode reader scanner registers a sealed closed package of bottles passing through on the assembled cartons shipping conveyor to identify and track the distribution of the batch identified product of one embodiment.

Product Labeling:

One embodiment of product labeling includes nutritional data is transmitted using the bamboo water bottling process server and computer for nutrients included in a product batch mixture. The bamboo water bottling process server calculates volumes of the nutrients in a batch mixture for inclusion in nutrition facts data to be included in a product batch label. The nutrition facts data can include for example a serving size 1 bottle up to 20 fl. oz., number of servings per container, total fat including saturated fat and trans fat, cholesterol, total carbohydrate, calories per serving, a % daily value calculated using the bamboo water bottling process server, sodium, total sugars including added sugars, protein, vitamins and minerals of one embodiment.

The bamboo water bottling process server can transmit the ingredients included in a product batch mixture. Each ingredient is listed in a descending order of predominance using the calculated volumes from the bamboo water bottling process server calculated volumes sorted by a descending order of predominance. The ingredients can for example include a common or usual name, the presence of any known major food allergen, an approved chemical preservative including a function of the preservatives, and certified colors and artificial colors. The bamboo water bottling process server can using language databases translate the ingredients, nutrients and other batch mixture data in a desired foreign language to create bilingual labeling with data in English first of one embodiment.

Information for products is included in creating label data. Label data can include for example a statement of product age for example of an alcoholic beverage showing "Aged 5 years". Label data can include for example a health warning statement, coloring, flavoring and blending materials, type of alcohol neutral spirits or distilled alcohol and whisky, beer, wine and name and address of the manufacturer, packer, or distributor of one embodiment.

Figure 13:
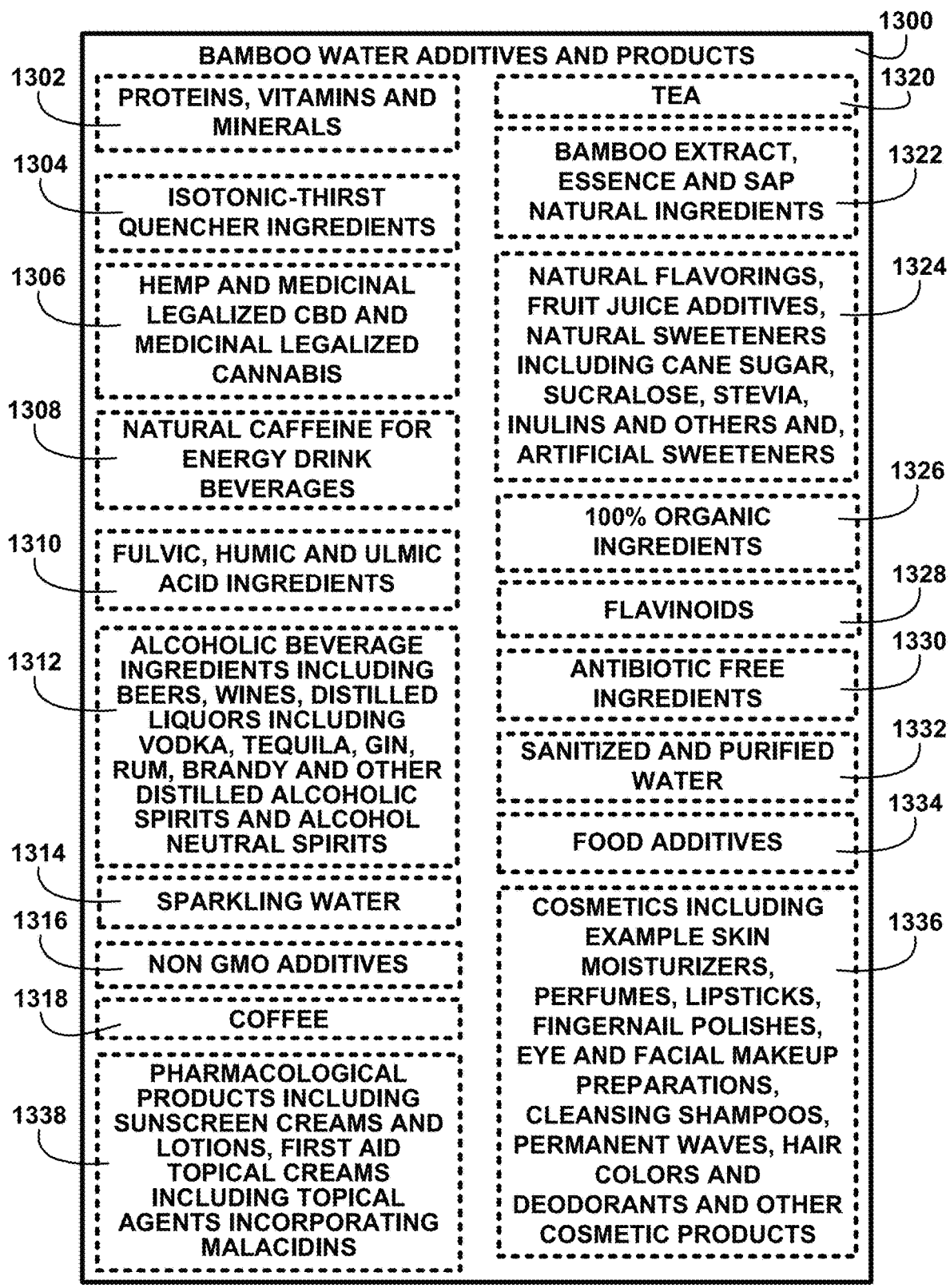
FIG. 13 shows a block diagram of an overview of bamboo water additives and products of one embodiment.

Bamboo Water Additives and Products:

FIG. 13 shows a block diagram of an overview of bamboo water additives and products of one embodiment. FIG. 13 shows examples of bamboo water additives and products 1300. The bamboo water additives and products 1300 include proteins, vitamins and minerals 1302, isotonic-thirst quencher ingredients 1304, hemp and medicinal legalized CBD and medicinal legalized cannabis 1306, natural caffeine for energy drink beverages 1308, fulvic, humic and ulmic acid ingredients 1310, alcoholic beverage ingredients including beers, wines, distilled liquors including vodka, tequila, gin, rum, brandy and other distilled alcoholic spirits and alcohol neutral spirits 1312, sparkling water 1314, non-GMO additives 1316, coffee 1318, tea 1320, bamboo extract, essence and sap natural organic ingredients 1322, natural flavorings, fruit juice additives, natural sweeteners including cane sugar, sucralose, *stevia*, inulins and others and, artificial sweeteners 1324, 100% organic ingredients 1326, flavinoids 1328, antibiotic free ingredients 1330, sanitized and purified water 1332 and food additives 1334.

Examples of bamboo water additives and products 1300 in addition to beverages include cosmetics including example skin moisturizers, perfumes, lipsticks, fingernail polishes, eye and facial makeup preparations, cleansing shampoos, permanent waves, hair colors and deodorants and other cosmetic products 1336 and pharmacological products including sunscreen creams and lotions, first aid topical creams including topical agents incorporating malacidins 1338. Examples of bamboo water additives and products 1300 not shown in FIG. 13 include food products that are enriched with bamboo extract, essence and sap natural ingredients 1322 for example protein bars, milk shake and malted shake mixes and drinks, fruit juices and drinks, baked goods mixes, prepared meals generally sold in the frozen food section, canned and bottled gravies, spaghetti, legumes, cookies, and other food stuffs wherein the bamboo extract, essence and sap natural ingredients 1322 are added and incorporated into the food preparation, dietary supplements including protein powders, multi-vitamin tablets and gummy products, weight loss products and other dietary supplement products.

Figure 14:
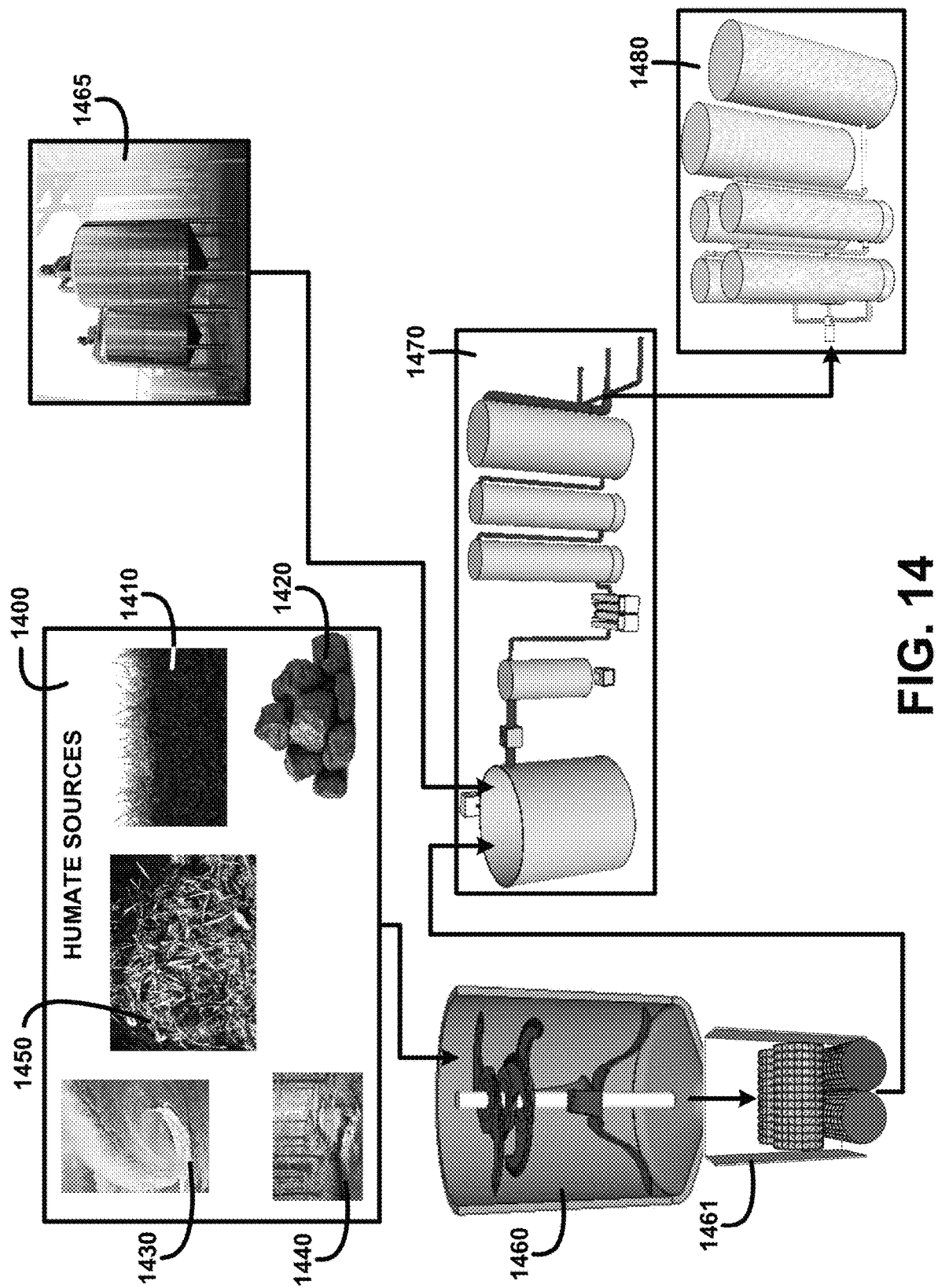
FIG. 14 shows a block diagram of an overview of black water humic and fulvic acids extraction for human consumption method and use and devices of one embodiment.

Humic and Fulvic Acids Extraction:

FIG. 14 shows a block diagram of an overview of black water humic and fulvic acids extraction for human consumption method and use and devices of one embodiment. FIG. 14 shows humate sources 1400 including humus soil 1410, coal 1420, ocean water 1430, inland stream 1440, degradated plants 1450 and composted plants 1455. Treated water storage 1465 contains a water source purified with various processes including filtration, ultrafiltration, purification, ultra-purification and sterilization that produce potable water. The treated water is mixed with at least one of the humate sources 1400 that have been processed using a humate materials chopper 1460 and chopped humate materials pulverizer 1461 in a mixing tank 1471.

The humate and treated water mixture filtration, dechlorination, defluoridation, sterilization, pH adjustment and temperature control devices and processes 1470 is followed by humic and fulvic acid molecules separation and segregated storage suspended in purified water 1480. The black water humic and fulvic acids extraction for human consumption and use method and devices processes and devices are controlled using digital processors, digital servers, digital computers, digital sensors, digital analyzers, digital valves, digital pumps, and other digitally controlled devices including wireless digital devices for automating individual process steps and operations. These processes produce humic and fulvic acids that are suitable for human consumption in for example a black colored water beverage, and other black colored water beverages including flavored beverages including a fruit flavored beverage, tea, coffee, soft drinks, alcoholic beverages, and products for human use including supplements, cosmetics, pharmaceuticals and food additives.

The humic and fulvic acids that are suitable for cosmetic products including for example skin moisturizers, perfumes, lipsticks, fingernail polishes, eye and facial makeup preparations, cleansing shampoos, permanent waves, hair colors and deodorants and other components used in cosmetic products. Hemp and medicinal legalized CBD and medicinal legalized cannabis are used in the solution for the human consumption beverages and the human use topical products for medicinal reasons. The humic and fulvic acids that are suitable for pharmacological products including for example fulvic sunscreen creams and lotions, fulvic first aid topical creams including fulvic topical agents to enhance healing of wounds infected with drug-resistant pathogens; and incorporating malacidins to attack and kill many types of super bugs, such as methicillin-resistant *Staphylococcus aureus* (MRSA) of one embodiment.

The foregoing has described the principles, embodiments and modes of operation of the embodiments. However, the embodiments should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A method, comprising:
   harvesting bamboo leaves from a bamboo forest;
   using hot air to sterilize the bamboo leaves in a step for drying the harvested bamboo leaves;
   shredding and packing the dry bamboo leaves;
   mixing sterilized water steam vapor and the shredded dry bamboo leaves for extracting a dry bamboo leaves essence into a bamboo leaf extract condensate;
   filtering the bamboo leaf condensate;
   mixing in purified water with the filtered bamboo leaf condensate;
   creating bamboo leaf extract based products from the mixed, filtered bamboo leaf condensate selected from the group consisting of bottled beverages, cosmetics, pharmaceuticals, foods, food additives and dietary supplements; and
   packaging the created bamboo leaf extract based products.

2. The method of claim 1, wherein the sterilizing and drying comprises harvested bamboo leaves being placed in a cage and rotating the cage while hot air is pumped into the rotating cage using an air heater.

3. The method of claim 1, wherein the shredding and packing dried and sterilized bamboo leaves comprises packing the leaves in aluminum bags and includes a step for identifying each of the aluminum bags with a unique barcode label for tracking of product ingredients through processing steps.

4. The method of claim 1, wherein extracting the dry bamboo leaves essence is performed by applying and mixing sterilized water steam vapor to the shredded dry bamboo leaves in a series of bamboo leaf-sterilized water steam brew tanks to create a bamboo leaves essence vapor and includes a final step for condensing bamboo extract vapors into the bamboo leaf extract condensate.

5. The method of claim 1, wherein the creating the bamboo leaf extract based products comprises producing at least one alcoholic drink beverage, optionally including vodka.

6. The method of claim 1, further comprising mixing in additives to the bamboo leaf extract condensate including at least one natural sweetener additive selected from the group consisting of *stevia* leaf extract, sweet proteins, synsepalum dulcificum berry, rebaudioside, erythritol, monk fruit, inulins, alcohol sugars, and natural sweeteners.

7. The method of claim 1, wherein the creating the bamboo leaf extract based products includes creating at least one cosmetics product selected from the group consisting of skin moisturizers, perfumes, lipsticks, fingernail polishes, eye and facial makeup preparations, cleansing shampoos, permanent waves, hair colors and deodorants.

8. The method of claim 1, wherein the creating the bamboo leaf extract based products includes creating at least one pharmaceuticals product to promote good health selected from the group consisting of sunscreen creams and lotions, first aid topical creams to enhance healing of wounds, and beverages with at least one medicinal additive selected from a group of hemp and medicinal legalized CBD, vitamins, minerals and fulvic and humic acids.

9. The method of claim 1, further comprising steps for monitoring sanitized conditions during creation and packaging of bottled beverage products during mixing and bottling processes using at least one testing device for detecting bacterial and microbial organisms selected from a group including heterotrophic plate count, coliforms, mold, yeast, *Pseudomonas aeruginosa*, bacteria, protozoa, fungi, viruses, and *E. coli*.

10. The method of claim 1, wherein the creating bamboo leaf extract based products includes creating at least one bottling bamboo water beverage mixture including a step for mixing in purified water, a step for mixing in additives including at least one flavoring for creating a flavored bamboo water beverage and optionally includes a step for mixing in carbonation for creating an effervescent bamboo water beverage.

11. An apparatus, comprising:
   a bamboo leaves drying machine for sterilizing and drying bamboo leaves;
   a bamboo leaves shredder hammer mill for shredding the dried bamboo leaves;
   an extraction machine for extracting the shredded, dried bamboo leaves and mixing the leaves with sterilized water steam vapor for providing an extracted bamboo leaf essence;
   a bamboo leaf essence vapor condensing device for condensed bamboo leaf essence vapors;

a condensate collection tank for collecting the condensed bamboo leaf essence vapors;

an aseptic filler for filling the bamboo leaf extract condensate into aseptic bags placed in a drum;

a sieves tower filtration device for filtering the bamboo leaf extract condensate and optionally collecting quality control samples; and a bamboo water bottling system for bottling filtered bamboo leaf extract condensate based beverages.

12. The apparatus of claim 11, wherein the bamboo leaves drying machine is configured to include an air heater coupled to a bamboo leaf cylindrical drying cage with a drying cage rotating drive motor.

13. The apparatus of claim 11, wherein the extraction machine is configured to include a sterilized water steam insulated pipeline coupled to a series of bamboo leaf-sterilized water steam brew tank devices.

14. The apparatus of claim 11, wherein the sieves tower filtration device is configured to include a vapor condensate sieves tower insulated inlet, a series of six diminishing mesh size filters with respective sieve filter mesh quality control outlets to fill respectively a quality control sample bag, and a bamboo leaf extraction condensate sieve collection chamber.

15. The apparatus of claim 11, wherein the bamboo water bottling system is configured for coupling to a bamboo leaf extraction network server coupled to a bamboo leaf extraction network computer with a bamboo water extraction process control application, and at least one digital processor controller coupled to digital sensors.

* * * * *